US008859197B2

(12) United States Patent
Moran et al.

(10) Patent No.: US 8,859,197 B2
(45) Date of Patent: Oct. 14, 2014

(54) SPERM-SPECIFIC CATION CHANNEL, CATSPER3, AND USES THEREFOR

(75) Inventors: Magdalene M. Moran, Brookline, MA (US); Jayhong A. Chong, Brookline, MA (US); Ian S. Ramsey, Boston, MA (US); David Clapham, Wellesley, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/361,426

(22) Filed: Jan. 30, 2012

(65) Prior Publication Data
US 2013/0072403 A1 Mar. 21, 2013

Related U.S. Application Data

(62) Division of application No. 10/523,479, filed as application No. PCT/US03/24432 on Aug. 4, 2003, now Pat. No. 8,110,668.

(60) Provisional application No. 60/401,863, filed on Aug. 7, 2002.

(51) Int. Cl.
*C12Q 1/00* (2006.01)
*C12Q 1/68* (2006.01)
*G01N 27/00* (2006.01)
*C07K 14/705* (2006.01)
*C12Q 1/02* (2006.01)
*C07K 14/00* (2006.01)
*A61K 38/00* (2006.01)

(52) U.S. Cl.
CPC ............. *C12Q 1/025* (2013.01); *A01K 2217/05* (2013.01); *C12Q 2600/156* (2013.01); *C12Q 1/6883* (2013.01); *A61K 38/00* (2013.01); *C07K 14/705* (2013.01)
USPC ................ 435/4; 435/6.1; 436/149; 530/350

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,459,039 | A | 10/1995 | Modrich et al. |
| 5,498,531 | A | 3/1996 | Jarrell |
| 6,159,478 | A | 12/2000 | Haanes et al. |
| 6,787,309 | B2 | 9/2004 | Splawski et al. |
| 8,110,668 | B2 | 2/2012 | Moran et al. |
| 2001/0039335 | A1 | 11/2001 | Jacobs et al. |
| 2002/0082210 | A1 | 6/2002 | Curtis |

FOREIGN PATENT DOCUMENTS

| | | |
|---|---|---|
| WO | WO-00/61624 | 10/2000 |
| WO | WO-00/66735 | 11/2000 |
| WO | WO-01/07611 | 2/2001 |
| WO | WO-01/54477 | 8/2001 |
| WO | WO-01/75067 | 10/2001 |
| WO | WO-01/88090 | 11/2001 |
| WO | WO-01/90304 | 11/2001 |
| WO | WO-02/090567 | 11/2002 |
| WO | WO-03/089583 | 10/2003 |
| WO | WO-03/091434 | 11/2003 |
| WO | WO-03/099865 | 12/2003 |

OTHER PUBLICATIONS

Arnoult, et al., "Activation of mouse sperm T-type Ca2+ channels by adhesion to the egg zona pellucida," Proc. Natl. Acad. Sci. USA, vol. 93, pp. 13004-13009, Nov. 1996.
Avidan et al., "Catsper2, a human autosomal nonsyndromic male infertility gene," European Journal of Human Genetics, 2003, 11:497-502.
Bedford, J.M., "Mammalian Fertilization Misread? Sperm Penetration of the Eutherian Zona Pellucida Is Unlikely to be a Lytic Event," Biology of Reproduction, vol. 59, pp. 1275-1287, 1998.
Chan H.C., Cation and anion channels in rat and human spermatozoa, Biochimica et Biophysica Acta, vol. 1323; pp. 117-129 (1997).
Colman, P.M., "Effects of amino acid sequence changes on antibody-antigen interactions," Research in Immunology, vol. 145; pp. 33-36 (1994).
Darszon, et al., "Ion Channels in Sperm Physiology," Physiological Reviews, vol. 79, No. 2, Apr. 1999, pp. 481-510.
Database EMBL, Oct. 11, 2001, XP002314905, Database Accession No. AAS90759.
Database EMBL, Sep. 11, 1997, XP002314902, Database Accession No. AA574312.
Database EMBL, Nov. 14, 1997, XP002314900, Database Accession No. AA662668.
Database EMBL, Dec. 2, 2000, XP002314901, Database Accession No. BF436942.
Database EMBL, Mar. 2, 2000, XP002314904, Database Accession No. AW472972.
Database EMBL, Oct. 20, 2000, XP002314898, Database Accession No. BF092492.

(Continued)

*Primary Examiner* — Ruixiang Li
(74) *Attorney, Agent, or Firm* — Wilmer Cutler Pickering Hale and Dorr LLP

(57) ABSTRACT

Nucleic acid and protein sequences relating to a cation channel which is sperm-specific (CatSper3) are disclosed. The CatSper3 protein is shown to be specifically expressed in sperm. Nucleic acids, vectors, transformed cells, transgenic animals, polypeptides, and antibodies relating to the CatSper3 gene and protein are disclosed. Also provided are methods of in vitro fertilization and contraception, methods of identifying modulators of CatSper3 activity, methods of genotyping subjects with respect to CatSper3, and methods of diagnosing and treating CatSper3-mediated disorders, including infertility. Related business methods are also disclosed.

10 Claims, 2 Drawing Sheets

(56) References Cited

OTHER PUBLICATIONS

Database EMBL, Jan. 25, 2001, XP002314968, Database Accession No. BF934163.
Database EMBL, Mar. 2, 2004, XP002314912, Database Accession No. ACN41330.
Database EMBL, Nov. 29, 2001, XP002314910, Database Accession No. ABL90376.
Database EMBL, Nov. 29, 2001, XP002314911, Database Accession No. ABB89967.
Database EMBL, Nov. 30, 1999, XP002314903, Database Accession No. AW197851.
Database EMBL, Jun. 8, 2000, XP002314899, Database Accession No. AW971983.
Database EMBL, Oct. 8, 2001, XP002314906, Database Accession No. B1826910.
Database EMBL, Oct. 8, 2001, XP002314907, Database Accession No. B1829451.
Database EMBL, May 9, 2001, XP002314908, Database Accession No. BG718343.
Database EMBL, Dec. 1, 2001, XP002306737, Database Accession No. Q96P76.
Database EMBL, Dec. 1, 2001, XP002306739, Database Accession No. Q91ZR5.
Database EMBL, Mar. 3, 2000, XP002306735, Database Accession No. AA416682.
Database EMBL, Mar. 3, 2000, XP002306736, Database Accession No. AA416577.
Database EMBL, May 30, 2000, XP002306734, Database Accession No. AP000586.
Database EMBL, May 9, 2001, XP002314909, Database Accession No. BG718245.
Database EMBL, Oct. 15, 2001, XP002306738, Database Accession No. AF407333.
Database EMBL, Oct. 15, 2001, XP002306740, Database Accession No. AF407332.
Garbers D.L., "Ion channels. Swimming with sperm," Nature, vol. 413, No. 6856, Oct. 2001, pp. 579, 581-582, XP 002314956.
Hillier et al., (1997) Accession No. AA416577.1. Accessed Oct. 29, 2010 at HTTp://www.nbci.nlm.nih.gov/nucest/AA416577.1?report=gbwithparts&log$=seqview.
Hillier et al., Accession No. AA41682.1 (1997).
Hyne and Garbers, "Calcium-dependent increase in adenosine 3', 5'-monophosphate and induction of the acrosome reaction in guinea pig spermatozoa," Proc. Natl. Acad. Sci. USA, vol. 76, No. 11, pp. 5699-5703, Nov. 1979.
Jin et al., "Catsper3 and Catsper4 encode two cation channel-like proteins exclusively expressedmin the testis," Biology of Reproduction, vol. 73, pp. 1235-1242 (2005).
Jungnickel, et al., "Trp2 regulates entry of Ca2+ into mouse sperm triggered by egg ZP3," Nature Cell Biology, vol. 3, May 2001, pp. 499-502.
Lehmann-Horn et al., "Voltage-Gated Ion Channels and hereditary disease," Physiol Rev, vol. 79(4), pp. 1317-1372 (1999).
Lobley et al., "Identification of human and mouse CatSper3 and Catspem4 genes: Characterisation of a common interaction domain and evidence for expression in testis," Reprod. Biol. Endocrinol., Aug. 1, 2003 1:53, 15 pages.
Martelange et al., "Identification on a Human Sarcoma of two new genes with tumor-specific expression," Cancer Research, vol. 60, pp. 3848-3855 (2000).
N. A., Suppl. 1, Trends Pharmacol Sci, vol. 18, pp. 77-84 (1997).
Nikpoor et al., "CatSper gene expression in postnatal development of mouse testis and in subfertile men deficient sperm motility," Human Reprod. vol. 19(1); pp. 124-128 (2004).
O'Toole, et al., "Ca2+ Entry through Store-operated Channels in Mouse Sperm Is Initiated by Egg ZP3 and Drives the Acrosome Reaction," Molecular Biology of the Cell, vol. 11, pp. 1571-1584, May 2000.
Quill, et al., "A voltage-gated ion channel expressed specifically in spermatozoa," PNAS, vol. 98, No. 22, 12527-12531, Oct. 23, 2001.
Ren et al., A Sperm Ion Channel Required for Sperm Motility and Male Fertility, Nature, Macmillian Journals Ltd., London, vol. 413, No. 6856, Oct. 11, 2001, pp. 603-609.
Sanger Centre, "Genome Sequence of the Nematode *C. elegans*: A Platform for investigating Biology," Science, vol. 282, pp. 2012-2018 (1998).
Santi, et al., "A dihydropyridine-sensitive T-type Ca2+ current is the main Ca2+ current carrier in mouse primary spermatocytes," American Journal of Physiology, vol. 271, pp. C1583-C1593, 1996.
Serrano, et al., "Voltage-dependent Ca2+ channel subunit expression and immunolocalization in mouse spermatogenic cells and sperm," FEBS Letters, 462, pp. 171-176, 1999.
Skolnick et al., "From genes to protein structure and function: novel applications of computational approaches in the genomic era," Trends in Biotechnology, 2000, 18:34-39.
Strausberg, R., *Homo sapiens*, Clone Image. Mar. 3, 2003, pp. 1-3, especially pp. 2-3.
Tash, Joseph S., "Role of the Camp, Calcium, and Protein Phosporylation in Sperm Motility," Controls of Sperm Motility: Biological and Clinical Aspects, eds. Gagnon, pp. 229-240, 1990.
Wassarman, et al., "A profile of fertilization in mammals," Nature Cell Biology, vol. 3, E59-E64, Feb. 2001.
Watson et al., Recombinant DNA, 2nd Edition, W.H. Freeman and Company, p. 107, (1992).
Wennemuth, et al., "Cav2.2 and Cav2.3 (N- and R-type) Ca2+ Channels in Depolarization-evoked Entry of Ca2+ into Mouse Sperm," The Journal of Biological Chemistry, vol. 275, No. 28, pp. 21210-21217, 2000.
Weyand, et al., "Cloning and functional expression of a cyclic nucleotide-gated channel from mammalian sperm," Nature, vol. 368, pp. 859-863, Apr. 28, 1994.
Whisstock et al., "Prediction of protein function from protein sequence and structure," Quarterly Review of Biophysics, 2003, 36:307-340.
Wiesner, et al., "Cyclic Nucleotide-gated Channels on the Flagellum Control of Ca2+ Entry into Sperm," The Journal of Cell Biology, vol. 142, No. 2, pp. 473-484, 1998.
Yanigimachi, R. "Mammalian Fertilization," The Physiology of Reproduction, Second Edition, eds. Knobil and Neill, pp. 189-317, 1994.

MSEKHKWWQQ VENIDITHLG PKRKAYELLG RHEEQVLINR RDVMEKKDAW 0050
DVQEFTQMY IKQLLRHPAF QLLLAFLLLS NAITIALRTN SYLGQKHYEL 0100
FSTIDDIVLT ILICEVLLGW LNGFWIFWKD GWNILNFAIV FILFMGFFIK 0150
QLDMVAITYP LRVLRLVHVC MAVEPLARII KVILQSMPDL ANVMALILFF 0200
MLVFSVFGVT LFGAFVPKHF QNMGVALYTL FICITQDGWL DIYTDFQMDE 0250
REYAMEVGGA IYFAVFITLG AFIGLNLFVV VVTTNLEQMM KTGEEEGHLN 0300
IKFTETEBDE DWTDELPLVH CTEARKDTST VPKEPLVGGP LSNLTEKTCD 0350
NFCLVLEAIQ ENLMEYKEIR EELNMIVEEV SSIRFNQEQQ NVILHKYTSK 0400
SATFLSEPPE GANKQDLITA LVSREKVSDS NINMVNKHKF SH 0442

FIG. 1

MRDNEKAWWQ QWTSHTGLEG WGGTQEDRMG FGGAVAALRG RPSPLQSTIH 0050
ESYGRPEEQV LINRQEITNK ADAWDMQEFI THMYIKQLLR HPAFQLLLAL 0100
LLVINAITIA LRTNSYLDQK HYELFSTIDD IVLTILLCEV LLGWLNGFWI 0150
FWKDGWNILN FIIVFILLLR FFINEINIPS INYTLRALRL VHVCMAVEPL 0200
ARIIRVILQS VPDMANIMVL ILFFMLVFSV FGVTLFGAFV PKHFQNIQVA 0250
LYTLFICITQ DGWVDIYSDF QTEKREYAME IGGAIYFTIF ITIGAFIGIN 0300
LFVIVVTTNL EQMMKAGEQG QQQRITFSET GAEBEEENDQ LPLVHCVVAR 0350
SEKSGLLQEP LAGGPLSNLS ENTCDNFCLV LEAIQENLRQ YKEIRDELNM 0400

FIG. 2

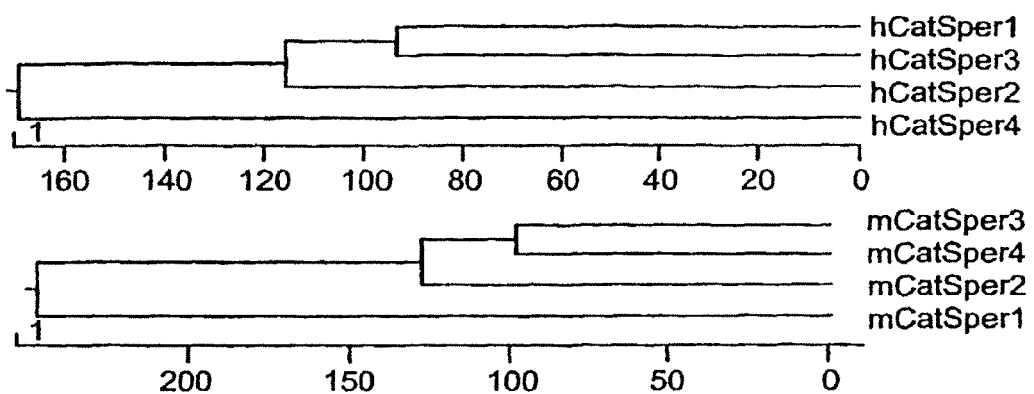

hCatSper3 and hCatSper1 are 21% identical
hCatSper3 and hCatSper2 are 22% identical
hCatSper4 and hCatSper1 are 17% identical
hCatSper4 and hCatSper2 are 21% identical mCatSper3 and mCatSper1 are 20% identical
mCatSper3 and mCatSper2 are 22% identical
mCatSper4 and mCarSper1 are 22% identical
mCatSper4 and mCatSper2 are 22% identical hCatSper1 and mCatSper1 are 48% identical
hCatSper2 and mCatSper2 are 71% identical
hCatSper3 and mCatSper3 are 68% identical
hCatSper4 and mCatSper4 are 65% identical

FIG. 3

SEQUENCE LISTING

```
<160> NUMBER OF SEQ ID NOS: 7

<210> SEQ ID NO 1
<211> LENGTH: 1203
<212> TYPE: DNA
<213> ORGANISM: Homo sapiens

<400> SEQUENCE: 1
atgagggata atgaaaaggc ctggtggcag caatggacct cccatacagg cctcgagggg       60
tggggcggga ctcaggagga ccgtatgggg tttggagggg cagtagctgc actgaggggc      120
cgcccctctc ccctgcagag taccattcac gagtcctacg gtcggccaga ggagcaagtg      180
ctcatcaacc gccaggaaat cacgaacaaa gcggacgcct gggacatgca ggagttcatc      240
actcacatgt acatcaagca gctgctccga caccccgcct tccaactgct gctggccctg      300
ctgctggtga tcaatgccat caccatcgct ctccgtacca actcctacct ggaccagaaa      360
cactatgagt tgttctctac catagatgac attgtgctga ccatccttct ttgtgaggtt      420
ctccttggct ggctcaatgg cttctggatt ttctggaagg acggctggaa catcctcaac      480
ttcattatcg tctttatctt gctcttgcgg ttcttcatta atgaaatcaa tattccctcc      540
atcaactaca ctctcagggc gcttcgtctg gtgcatgtgt gcatggcggt ggagcccctc      600
gcccggatca tccgcgtcat cctgcagtcg gtgcctgaca tggccaatat catggtcctc      660
atcctcttct tcatgctggt tttttccgtg tttggagtaa cactctttgg tgcattcgtg      720
cccaagcatt tccagaacat acaggttgcg ctgtacaccc tcttcatctg catcacccag      780
gacggctggg tggacatcta cagtgacttc cagacagaga gagggaata tgcaatggag      840 attggggggtg ccatctactt taccatcttc atcaccatcg gtgccttcat ggcatcaac      900 ctgttcgtca tcgtggtgac caccaacctg gagcaaatga tgaaggcagg agagcaggga      960
caacagcaac gaataacctt tagtgagaca ggcgcagagg aagaggagga gaatgaccag     1020
ctgccactgg tgcattgtgt ggtcgcccgc tcggagaaat ctggtctcct ccaggaaccc     1080
cttgcgggag gccccctgtc gaacctctca gaaaacacgt gtgacaactt ttgcttggtg     1140
cttgaggcaa tacaggagaa cctgaggcag tacaaggaga tccgagatga actcaacatg     1200
tag                                                                   1203

<210> SEQ ID NO 2
<211> LENGTH: 400
<212> TYPE: PRT
<213> ORGANISM: Homo sapiens

<400> SEQUENCE: 2

Met Arg Asp Asn Glu Lys Ala Trp Trp Gln Gln Trp Thr Ser His Thr
  1               5                  10                  15

Gly Leu Glu Gly Trp Gly Gly Thr Gln Glu Asp Arg Met Gly Phe Gly
             20                  25                  30

Gly Ala Val Ala Ala Leu Arg Gly Arg Pro Ser Pro Leu Gln Ser Thr
         35                  40                  45
```

Ile His Glu Ser Tyr Gly Arg Pro Glu Glu Gln Val Leu Ile Asn Arg
 50                  55                  60

Gln Glu Ile Thr Asn Lys Ala Asp Ala Trp Asp Met Gln Glu Phe Ile
 65                  70                  75                  80

Thr His Met Tyr Ile Lys Gln Leu Leu Arg His Pro Ala Phe Gln Leu
                 85                  90                  95

Leu Leu Ala Leu Leu Val Ile Asn Ala Ile Thr Ile Ala Leu Arg
            100                 105                 110

Thr Asn Ser Tyr Leu Asp Gln Lys His Tyr Glu Leu Phe Ser Thr Ile
        115                 120                 125

Asp Asp Ile Val Leu Thr Ile Leu Leu Cys Glu Val Leu Leu Gly Trp
130                 135                 140

Leu Asn Gly Phe Trp Ile Phe Trp Lys Asp Gly Trp Asn Ile Leu Asn
145                 150                 155                 160

Phe Ile Ile Val Phe Ile Leu Leu Arg Phe Phe Ile Asn Glu Ile
                165                 170                 175

Asn Ile Pro Ser Ile Asn Tyr Thr Leu Arg Ala Leu Arg Leu Val His
                180                 185                 190

Val Cys Met Ala Val Glu Pro Leu Ala Arg Ile Ile Arg Val Ile Leu
            195                 200                 205

Gln Ser Val Pro Asp Met Ala Asn Ile Met Val Leu Ile Leu Phe Phe
210                 215                 220

Met Leu Val Phe Ser Val Phe Gly Val Thr Leu Phe Gly Ala Phe Val
225                 230                 235                 240

Pro Lys His Phe Gln Asn Ile Gln Val Ala Leu Tyr Thr Leu Phe Ile
                245                 250                 255

Cys Ile Thr Gln Asp Gly Trp Val Asp Ile Tyr Ser Asp Phe Gln Thr
                260                 265                 270

Glu Lys Arg Glu Tyr Ala Met Glu Ile Gly Gly Ala Ile Tyr Phe Thr
            275                 280                 285

Ile Phe Ile Thr Ile Gly Ala Phe Ile Gly Ile Asn Leu Phe Val Ile
        290                 295                 300

Val Val Thr Thr Asn Leu Glu Gln Met Met Lys Ala Gly Glu Gln Gly
305                 310                 315                 320

Gln Gln Gln Arg Ile Thr Phe Ser Glu Thr Gly Ala Glu Glu Glu
                325                 330                 335

Glu Asn Asp Gln Leu Pro Leu Val His Cys Val Val Ala Arg Ser Glu
            340                 345                 350

Lys Ser Gly Leu Leu Gln Glu Pro Leu Ala Gly Gly Pro Leu Ser Asn
        355                 360                 365

Leu Ser Glu Asn Thr Cys Asp Asn Phe Cys Leu Val Leu Glu Ala Ile
    370                 375                 380

Gln Glu Asn Leu Arg Gln Tyr Lys Glu Ile Arg Asp Glu Leu Asn Met
385                 390                 395                 400

<210> SEQ ID NO 3
<211> LENGTH: 1329
<212> TYPE: DNA
<213> ORGANISM: Mus sp.

<400> SEQUENCE: 3
atgtctgaaa acacaagtg gtggcagcag gtggagaaca tcgacatcac acacctgggc    60
cctaagagaa aagcctatga actcctgggt cggcatgagg agcaagtgct catcaaccgc   120

| | |
|---|---|
| agagatgtca tggagaagaa ggatgcctgg gatgtacagg aattcatcac tcaaatgtat | 180 |
| atcaagcagt tgctccgcca tccggccttc cagctgctgc tggcctttct gctgctgtcc | 240 |
| aacgccatca ccattgccct tcgcaccaac tcttatctcg gtcagaaaca ctacgagcta | 300 |
| ttctcgacca tagatgacat tgtgttgacg atccttatct gcgaggttct gcttggttgg | 360 |
| cttaacggct ctggatttt ctggaaggat ggctggaata tcctcaactt cgcaattgtc | 420 |
| tttatcttgt ttatggggtt cttcataaaa caacttgaca tggttgccat cacctaccct | 480 |
| ctcagggtgc tccggctggt gcatgtgtgt atggcggtgg aaccctggc cagaatcatc | 540 |
| aaggttatcc tgcagtcgat gccagacttg gccaatgtca tggctctcat cctcttcttc | 600 |
| atgctggtat tctctgtgtt tggggtcacg ctcttcggtg catttgtgcc caagcatttc | 660 |
| cagaacatgg gggttgccct gtacacgctc ttcatctgca tcactcagga tggatggctg | 720 |
| gacatctaca ctgacttcca gatggatgaa agagagtacg cgatggaggt cggggggcgcc | 780 |
| atctactttg ccgtctttat caccctcggt gccttcattg gtctcaactt gttcgtcgtc | 840 |
| gtggtgacca caaacctgga acaaatgatg aagaccggcg aggaagaggg acacctgaac | 900 |
| ataaagttta ctgagacaga agaggatgag gactggaccg acgagctgcc actggtgcat | 960 |
| tgtacagagg cccgcaagga tacttccact gtccccaagg aaccactggt tgggggcccc | 1020 |
| ctgagtaacc tcacagaaaa gacctgcgat aacttctgct tggtgcttga agcaatacag | 1080 |
| gagaacttga tggagtacaa agagatccga gaggaactca acatgatcgt ggaggaagtg | 1140 |
| tcctccatcc ggttcaacca ggagcagcaa aatgtgatcc tacacaagta tacctccaaa | 1200 |
| agcgccacct tcctaagcga gcccccagaa ggggctaaca agcaagactt gatcactgcg | 1260 |
| ctggtcagca gggaaaaggt gtctgattct aacataaaca tggttaacaa acacaagttc | 1320 |
| agccactga | 1329 |

<210> SEQ ID NO 4
<211> LENGTH: 442
<212> TYPE: PRT
<213> ORGANISM: Mus sp.

<400> SEQUENCE: 4

Met Ser Glu Lys His Lys Trp Trp Gln Gln Val Glu Asn Ile Asp Ile
1               5                   10                  15

Thr His Leu Gly Pro Lys Arg Lys Ala Tyr Glu Leu Leu Gly Arg His
            20                  25                  30

Glu Glu Gln Val Leu Ile Asn Arg Arg Asp Val Met Glu Lys Lys Asp
        35                  40                  45

Ala Trp Asp Val Gln Glu Phe Ile Thr Gln Met Tyr Ile Lys Gln Leu
    50                  55                  60

Leu Arg His Pro Ala Phe Gln Leu Leu Leu Ala Phe Leu Leu Leu Ser
65                  70                  75                  80

Asn Ala Ile Thr Ile Ala Leu Arg Thr Asn Ser Tyr Leu Gly Gln Lys
                85                  90                  95

His Tyr Glu Leu Phe Ser Thr Ile Asp Asp Ile Val Leu Thr Ile Leu
            100                 105                 110

Ile Cys Glu Val Leu Leu Gly Trp Leu Asn Gly Phe Trp Ile Phe Trp
        115                 120                 125

Lys Asp Gly Trp Asn Ile Leu Asn Phe Ala Ile Val Phe Ile Leu Phe
    130                 135                 140

Met Gly Phe Phe Ile Lys Gln Leu Asp Met Val Ala Ile Thr Tyr Pro
145                 150                 155                 160

```
Leu Arg Val Leu Arg Leu Val His Val Cys Met Ala Val Glu Pro Leu
                165                 170                 175
Ala Arg Ile Ile Lys Val Ile Leu Gln Ser Met Pro Asp Leu Ala Asn
            180                 185                 190
Val Met Ala Leu Ile Leu Phe Phe Met Leu Val Phe Ser Val Phe Gly
        195                 200                 205
Val Thr Leu Phe Gly Ala Phe Val Pro Lys His Phe Gln Asn Met Gly
    210                 215                 220
Val Ala Leu Tyr Thr Leu Phe Ile Cys Ile Thr Gln Asp Gly Trp Leu
225                 230                 235                 240
Asp Ile Tyr Thr Asp Phe Gln Met Asp Glu Arg Glu Tyr Ala Met Glu
                245                 250                 255
Val Gly Gly Ala Ile Tyr Phe Ala Val Phe Ile Thr Leu Gly Ala Phe
            260                 265                 270
Ile Gly Leu Asn Leu Phe Val Val Val Thr Thr Asn Leu Glu Gln
        275                 280                 285
Met Met Lys Thr Gly Glu Glu Glu Gly His Leu Asn Ile Lys Phe Thr
    290                 295                 300
Glu Thr Glu Glu Asp Glu Asp Trp Thr Asp Glu Leu Pro Leu Val His
305                 310                 315                 320
Cys Thr Glu Ala Arg Lys Asp Thr Ser Thr Val Pro Lys Glu Pro Leu
                325                 330                 335
Val Gly Gly Pro Leu Ser Asn Leu Thr Glu Lys Thr Cys Asp Asn Phe
            340                 345                 350
Cys Leu Val Leu Glu Ala Ile Gln Glu Asn Leu Met Glu Tyr Lys Glu
        355                 360                 365
Ile Arg Glu Glu Leu Asn Met Ile Val Glu Val Ser Ser Ile Arg
    370                 375                 380
Phe Asn Gln Glu Gln Gln Asn Val Ile Leu His Lys Tyr Thr Ser Lys
385                 390                 395                 400
Ser Ala Thr Phe Leu Ser Glu Pro Pro Glu Gly Ala Asn Lys Gln Asp
                405                 410                 415
Leu Ile Thr Ala Leu Val Ser Arg Glu Lys Val Ser Asp Ser Asn Ile
            420                 425                 430
Asn Met Val Asn Lys His Lys Phe Ser His
        435                 440

<210> SEQ ID NO 5
<211> LENGTH: 2079
<212> TYPE: DNA
<213> ORGANISM: Homo sapiens

<400> SEQUENCE: 5
gggctgccgg gggtaggagg tggggataaa caacagggcg tggagctcag acagaaaccc     60
tctgtgcttt ccaccctgcc tgcagcccag ccctgctcaa gctggagtc ccctccatgg    120 agacacatca cctgcagcca cccccacaca gcgcagccca cggacctcct ttggctctct    180
gacaggtgct gggctggagt tgggagctgg gctgggggct ggggtgggca catcctcatc    240
ctgctcttcc ctcccacaga cagcagtgaa gaggcactgg aaggaatggt acggggggctg    300 aggcagggtg gcgtgtccct cctaggccag ccacagcccc tgacccagga cagtggcgg    360 agctctttca tgcggcgcaa ccgagaccct cagctcaatg agcgagtgca ccgtgtgcgg    420
gcgctacaga gcacactcaa ggtcagctgg ggggctctgg gcacagcaag ggactaggct    480
```

| | |
|---|---|
| ctgggcttca ggctttggtt tgcggctgtc acctccaccc tgggcaccag actccagact | 540 |
| ccagactcag ctccggaccc tgggcttagc agctgacagc gggctcagct gtggactggg | 600 |
| ccaggctctg ggttccgagt ggggatttga gtctcaccta ggctcctcgt gccacgctgg | 660 |
| ccaggtgctg gcttccaggc accggacctc cggagtgaag tctggcctcg gctctgccc | 720 |
| acttccctgg gtgatcatgg tcccttagcc cctcctctcc acacaggcaa agctgcagga | 780 |
| gctgcaggtc ctagaagaag tgctgggtga ccctgagctg acaggagaga agttccgcca | 840 |
| gtggaaggag cagaaccggg agctgtactc agagggcctg ggggcctggg gagtggcaca | 900 |
| ggctgaaggc agctcccaca tcttgacctc tgactccaca gaacagtccc cccactccct | 960 |
| gccctctgac cctgaagagc actcccatct ctgcccctg acctcagaga gcagcctccg | 1020 |
| acctcctgac ctctgaccct ggccagcact ctagctcctg acctttgacc cgagggccac | 1080 |
| ctcaaccca gcttctgacg tgtccaggac agagcatccc tggattctgt tcagggtggg | 1140 |
| aagtagtact gctagtcatg gtctcacccc gagctgaccc ctctgcctgg gctttgtgcc | 1200 |
| accctctccc ttgccaaaga agaaactctc ccccaaatc ctccaacctc tggggccaca | 1260 |
| gccctgcccc tccagttcct tggcagttct ccccaaacc aggtctgtac aggtgttctt | 1320 |
| tattttacat gagggctact ttccaaccaa ataaagtcaa tttttctaag aatgagtcta | 1380 |
| catgtaactt tacttccata ttcgaattgg aaatctgccc ccctgtgggg actgggtga | 1440 |
| gtgctcttgg ccagagggtg ggtggcagac ccttcgtgca gcccgttggc ctgggctctg | 1500 |
| tacccgagct ccaagcctgc caggatggtg ggggatgacc catggctaat gagggctccg | 1560 |
| actcatgtcc acctctcccc agctctttga aggctaatgg tgatctccta ccccattccc | 1620 |
| gggggggcaca caatgagaaa cttccacttt gtagatgggg aaatgcactt tgcacggaaa | 1680 |
| ggtggtgggg acagtcctgg agactgggct ggtaggacag ggcagctggt ggggaagggt | 1740 |
| gcaggttgag gtctgccctg ggaaggccct ggggaaaaca cttctctcct tcactcctca | 1800 |
| ttccagcctc acctccacct cctggatcca aggcagggac atgtccctgt gactccattc | 1860 |
| aggctgcacg ggaaatctga cctgctccca tcagcctctg acttccaacc ccagcccagc | 1920 |
| atccccacag catccccaga cttcctctgt gggatgcgga ggagggccaa tgggaggagc | 1980 |
| ttctctccag gttggaattc ctcagtagaa tgcagacggc tggaggtcac agaggcctct | 2040 |
| gtgatatcac cacgaggggg agtgagacca cttggagtg | 2079 |

<210> SEQ ID NO 6
<211> LENGTH: 36
<212> TYPE: DNA
<213> ORGANISM: Homo sapiens

<400> SEQUENCE: 6

| | |
|---|---|
| aagattcttt gaggagaagg aagagactga gcaaac | 36 |

<210> SEQ ID NO 7
<211> LENGTH: 478
<212> TYPE: DNA
<213> ORGANISM: Homo sapiens

<400> SEQUENCE: 7

| | |
|---|---|
| gggagggtac tggggctgcc cccaagtcat gtgagtcaag gctgggcgga gcgtcagagt | 60 |
| cttctggcct tcacgccctc accatttata aggcagagcc tggcccccac agaggtcccc | 120 |
| caccctattg gtgaggaac tggaatccag actccaggtt ccttccatct cacacaaggg | 180 |
| cacagctcgg cctgggtctc tgtcagggct gcgtgggaga gcgaagcggg ggtgacgcca | 240 |

```
gggaagaggt gggagggctg cttccctccc ctgaggcctt ctgaaaggca ctcactgctc    300
cacccccagg attgtggagg aggtgcgtgc aatccgcttc aaccaggagc aggagtcaga    360
ggtgttgaac aggcgctcgt cgacgagcgg gtcgttggag actacgtcat ccaaggacat    420
ccgccagatg tctcaacagc aagacttgct cagtgcgctc gttagcatgg aaaaggtg     478
```

SPERM-SPECIFIC CATION CHANNEL, CATSPER3, AND USES THEREFOR

RELATED APPLICATIONS

This application is a divisional of U.S. application Ser. No. 10/523,479, filed Sep. 16, 2005, which claims the benefit of priority of PCT International Application No. PCT/US2003/024432 filed Aug. 4, 2003, which claims the benefit of priority of U.S. Provisional Application Ser. No. 60/401,863, filed Aug. 7, 2002, the entire contents of which are hereby incorporated by reference herein.

BACKGROUND OF THE INVENTION

1. Field of the Invention

The present invention relates to the fields of molecular biology, and reproductive technology. In particular, the invention relates to a cation channel protein expressed specifically in sperm cells, to nucleic acids encoding the protein, cells engineered to express the protein, assays for compounds affecting the activity of the protein, and to the use of such compounds in the treatment or causation of infertility, or as a means of contraception or animal control.

2. Description of the Related Art

Sperm and ova reciprocally interact in mammalian fertilization (Wassarman, et al. (2001), *Nature Cell Biology* 3, E59-E64; Yanagimachi (1994), in *The Physiology of Reproduction*, eds. Knobil & Neill (Raven Press, New York), pp. 189-315). To reach the site of fertilization, sperm must travel relatively long distances and become primed for fertilization of the ova through capacitation and other processes. Once they arrive at the surface of an ovum, sperm interact with ovum extracellular matrix glycoproteins including the zona pellucida proteins. Sperm release acidic material during the acrosome reaction, a signaling event that presumably involves the opening of $Ca^{2+}$ channels and the influx of $Ca^{2+}$ into the sperm heads (O'Toole, et al. (2000), *Mol Biol Cell* 11, 1571-84). The TRPC2 protein, a putative $Ca^{2+}$-permeant channel, has recently been implicated in the acrosome reaction (Jungnickel, et al. (2001), *Nat Cell Biol* 3, 499-502). Penetration of sperm through the thick outer layer of the ovum is achieved through chemical lysis of the ovum coat and/or the mechanical motion of sperm (Bedford (1998), *Biol Reprod* 59, 1275-87). Following infiltration of the ovum ZP coat, the sperm membrane fuses with that of ovum. Fusion is followed by activation of the fertilization process, beginning with $Ca^{2+}$ oscillations in the ovum (Wassarman, et al. (2001), *Nature Cell Biology* 3, E59-E64; Yanagimachi (1994), in *The Physiology of Reproduction*, eds. Knobil & Neill (Raven Press, New York), pp. 189-315).

$Ca^{2+}$ and cyclic nucleotides control sperm motility (Tash (1990) in *Controls of Sperm Motility: biological and clinical aspects*, ed. Gagnon (CRC Press, Boca Raton), pp. 229-240; Darszon, et al. (1999), *Physiol Rev* 79, 481-510; Hyne & Garbers (1979), *Proc Natl Acad Sci USA* 76, 5699-703) and several voltage-dependent $Ca^{2+}$ channel ($Ca_V$) mRNAs and cyclic nucleotide-gated (CNG) channel proteins have been detected in sperm cell precursors (Darszon, et al. (1999), *Physiol Rev* 79, 481-510; Serrano, et al. (1999), *FEBS Lett* 462, 171-6; Weyand, et al. (1994) *Nature* 368, 859-63; Wiesner, et al. (1998), *J Cell Biol* 142, 473-84). Furthermore, low voltage activated, dihydropyridine-sensitive "T-type" channels (Santi, et al. (1996), *Am J Physiol* 271, C1583-93; Arnoult, et al. (1996), *Proc Natl Acad Sci USA* 93, 13004-9) and pharmacologically defined N- and R-type currents have been measured in spermatogenic cells (Wennemuth, et al. (2000), *J Biol Chem* 275, 21210-7). But the role of these channels in spermatogenesis or mature sperm function is not known.

Two sperm-specific cation channels, designated CatSper1 and CatSper2, have previously been described (Ren et al. (2001), *Nature* 413:603-9; Quill et al. (2001), *Proc. Natl. Acad. Sci. (USA)* 98(22): 12527-31). These proteins are the subject of U.S. Prov. Appln. Ser. No. 60/288,402, filed May 3, 2001, U.S. Prov. Appln. Ser. No. 60/327,167, filed Oct. 4, 2001, U.S. Prov. Appln. Ser. No. 60/345,324, filed Oct. 22, 2001, and PCT Intl. Appln. No. PCT/US02/13487, filed May 3, 2002,

SUMMARY OF THE INVENTION

In one aspect, the present invention provides isolated nucleic acids corresponding to all or a portion of a CatSper3 gene. In some embodiments, the isolated nucleic acids include a nucleotide sequence of at least 10, 12, 14, 16 or 18 consecutive nucleotides of SEQ ID NO: 1 or SEQ ID NO: 3, or a sequence complementary thereto. In other embodiments, the nucleic acids include nucleotide sequences encoding a CatSper3 protein, at least a transmembrane domain of a CatSper3 protein, at least an extracellular loop of a CatSper3 protein, at least a pore region of a CatSper3 protein, at least an epitope of a CatSper3 protein having high predicted antigenicity, or a sequence complementary thereto. In particular embodiments, the nucleic acids include a sequence of SEQ ID NO: 1; a sequence of SEQ ID NO: 3; a sequence encoding a polypeptide comprising residues 88-117, 128-152, 155-180, 217-242, 245-268 and 282-308 of SEQ ID NO: 2; a sequence encoding a polypeptide comprising residues 64-95, 101-129, 131-178, 191-218, 221-246 and 259-284 of SEQ ID NO: 4; a sequence encoding a polypeptide comprising residues 118-127, 181-216 and 269-281 of SEQ ID NO: 2; a sequence encoding a polypeptide comprising residues 96-100, 179-190 and 247-258 of SEQ ID NO 4; a sequence encoding a polypeptide comprising residues 257-265 of SEQ ID NO: 2; a sequence encoding a polypeptide comprising residues approximately residues 234-241 of SEQ ID NO: 4; a sequence encoding a polypeptide comprising a high predicted antigenicity epitope of SEQ ID NO: 2; a sequence encoding a polypeptide comprising a high predicted antigenicity epitope (e.g., residues 386-407) of SEQ ID NO: 4; and a sequence complementary thereto.

In another aspect, the invention provides isolated nucleic acids encoding polypeptide having at least 80%, 85%, 90%, or 95% amino acid sequence identity with a CatSper3 protein; at least a transmembrane domain of a CatSper3 protein; at least an extracellular loop of a CatSper3 protein; and at least a pore region of a CatSper3 protein. In some embodiments, the isolated nucleic acids encode a polypeptide having at least 80%, 85%, 90% or 95% amino acid sequence identity with a CatSper3 protein and having CatSper3 activity in a cell capable of expressing CatSper3 activity. In some embodiments, the isolated nucleic acids include a regulatory element having at least 80%, 85%, 90% or 95% nucleotide sequence identity to at least 100, 200, 300 or 400 consecutive nucleotides from SEQ ID NO: 5, and that is capable of promoting transcription of a coding sequence operably joined thereto in a mammalian cell in which a CatSper3 gene can be expressed.

In another aspect, the invention provides isolated nucleic acids that hybridize to at least a portion of a nucleic acid of SEQ ID NO: 1 or SEQ ID NO: 3 under conditions including a wash step of 1.0×SSC at 65° C., a wash step of 0.5×SSC, a wash step of 0.2×SSC, or a wash step of 0.1×SSC. In some embodiments, the isolated nucleic acids encode a polypeptide having CatSper3 activity.

In another aspect, the invention provides nucleic acid comprising a nucleotide sequence encoding a polypeptide having CatSper3 activity, and that hybridizes to at least a portion of a nucleic acid of SEQ ID NO: 1 or SEQ ID NO: 3 under conditions including a wash step of 1.0×SSC at 65° C., a wash step of 0.5×SSC, a wash step of 0.2×SSC, or a wash step of 0.1×SSC; and that is operably joined to a heterologous regulatory region such that the sequence is expressed. In another embodiment, the invention provides a nucleic acid comprising a nucleotide sequence encoding a polypeptide having at least 80%, 85%, 90% or 95% amino acid sequence identity with an amino acid sequence of SEQ ID NO: 2 or 4; and is operably joined to a heterologous regulatory region such that the sequence is expressed.

In another aspect, the invention provides a kit for detecting at least a portion of a CatSper3 nucleic acid. The kits can include any of the foregoing isolated nucleic acids of the invention, and a means for detecting the isolated nucleic acid. In some embodiments, the means for detecting the isolated nucleic acid includes a detectable label bound thereto and, in some embodiments, the means includes a labeled secondary nucleic acid which specifically hybridizes to the first isolated nucleic acid.

In another aspect, the invention provides vectors including any of the foregoing isolated nucleic acids of the invention. In some embodiments, the vector includes a genetic construct capable of expressing the nucleic acids of the invention. In some embodiments, the nucleic acids of the invention are operably joined to an exogenous regulatory region and, in some embodiments, the nucleic acids are operably joined to heterologous coding sequences to form a fusion vector. In some embodiments, the vector includes a CatSper3 regulatory region and, in some embodiments, the CatSper3 regulatory region is operably joined to a heterologous coding sequence.

In another aspect, the invention provides cells transformed with the foregoing nucleic acids of the invention, or a genetic construct capable of expressing a nucleic acid of the invention. In some embodiments, the nucleic acid of the invention is operably joined to heterologous coding sequences to encode a fusion protein. In some embodiments, the cells are bacterial cells, yeast cells, insect cells, nematode cells, amphibian cells, rodent cells, or human cells. In some embodiments, the cells are mammalian somatic cells, fetal cells, embryonic stem cells, zygotes, gametes, germ line cells and transgenic animal cells.

In another aspect, the invention provides non-human transgenic animals. In these aspects, a genetic construct has introduced a modification into a genome of the animal, or an ancestor of the animal, and the modification includes insertion of a nucleic acid encoding at least a fragment of a CatSper3 protein, inactivation of an endogenous CatSper3 gene, or insertion by homologous recombination of a reporter gene operably joined to CatSper3 regulatory elements. In some embodiments, the modification is insertion of nucleic acid encoding a CatSper3 protein, at least a transmembrane domain of a CatSper3 protein, at least an extracellular loop of a CatSper3 protein, at least a pore region of a CatSper3 protein, or at least an epitope of a CatSper3 protein having high predicted antigenicity. In some embodiments, the animals are rats, mice, hamsters, guinea pigs, rabbit, dogs, cats, goats, sheep, pigs, and non-human primates.

In another aspect, the invention provides substantially pure protein preparations including polypeptides selected from a CatSper3 protein; at least a transmembrane domain of a CatSper3 protein; at least an extracellular loop of a CatSper3 protein; at least a pore region of a CatSper3 protein; and at least an epitope of a CatSper3 protein having high predicted antigenicity. In particular embodiments, the polypeptide is selected from SEQ ID NO: 2; SEQ ID NO: 4; residues 88-117, 128-152, 155-180, 217-242, 245-268 and 282-308 of SEQ ID NO: 2; residues 64-95, 101-129, 131-178, 191-218, 221-246 and 259-284 of SEQ ID NO: 4; residues 118-127, 181-216 and 269-281 of SEQ ID NO: 2; residues 96-100, 179-190 and 247-258 of SEQ ID NO 4; residues 257-265 of SEQ ID NO: 2; residues 234-241 of SEQ ID NO: 4; a high predicted antigenicity epitope of SEQ ID NO: 2; and a high predicted antigenicity epitope (e.g., residues 386-407) of SEQ ID NO: 4.

In another aspect, the invention provides a substantially pure protein preparation including polypeptides having at least 80%, 85%, 90%, or 95% amino acid sequence identity with a CatSper3 protein; at least a transmembrane domain of a CatSper3 protein; at least an extracellular loop of a CatSper3 protein; or at least a pore region of a CatSper3 protein. In some embodiments, the substantially pure protein preparation includes a polypeptide having at least 80%, 85%, 90%, or 95% amino acid sequence identity with a CatSper3 protein and having CatSper3 activity in a cell capable of expressing CatSper3 activity.

In another aspect, the invention provides a substantially pure antibody preparation including an antibody raised against a CatSper3 epitope. In some embodiments, the epitope has high predicted antigenicity. In some embodiments, the epitope includes an amino acid sequence within a high predicted antigenicity epitope of SEQ ID NO: 2, and a high predicted antigenicity epitope (e.g., residues 386-407) of SEQ ID NO: 4. In some embodiments, the antibody is a monoclonal antibody. In some embodiments, antibody is an Fab fragment, an F(ab')2 fragment, an Fv fragment, or a single-chain Fv fragment (scFv).

In another aspect, the invention provides a kit for detecting at least an epitope of a CatSper3 protein. The kits include an anti-CatSper3 antibody of the invention and a means for detecting said antibody. In some embodiments, the means for detecting said anti-CatSper3 antibody includes a detectable label bound thereto and, in some embodiments, the means for detecting said anti-CatSper3 antibody includes a labeled secondary antibody which specifically binds to the anti-CatSper3 antibody.

In another aspect, the invention provides methods of identifying potential modulators of CatSper3 activity. The methods include contacting a candidate compound with a cell expressing a CatSper3 protein; measuring an indicator of CatSper3 activity in the cell; determining whether the candidate compound caused an increase or decrease in the indicator relative to a reference level; and identifying the candidate compound as a potential modulator of CatSper3 activity if the increase or decrease is significant. In some embodiments, the indicator is an indicator of the level of mRNA encoding the CatSper3 protein, an indicator of the level of CatSper3 protein, an indicator of cation flux across a membrane of said cell, or an indicator of whole cell or channel currents of said cell. In some embodiments, the cell has been transformed with a genetic construct capable of expressing a CatSper3 protein. In some embodiments, the cell is a mature sperm cell and the indicator is a measure of sperm motility.

In another aspect, the invention provides methods of identifying a potential modulator of CatSper3 activity comprising contacting a candidate compound with at least a structural domain of a CatSper3 protein; measuring binding, if any, between the candidate compound and the CatSper3 moiety; and identifying the candidate compound as a potential modulator of CatSper3 activity if the binding is significant. In some embodiments, the CatSper3 moiety is a CatSper3 protein; at least a transmembrane domain of a CatSper3 protein; at least an extracellular loop of a CatSper3 protein; or at least a pore region of a CatSper3 protein.

In another aspect, the invention provides a method of decreasing the fertility of a male subject by administering a compound to the subject which decreases CatSper3 activity. In another aspect, the invention provides a method of causing reversible infertility in a male subject by administering to a compound to the subject which decreases CatSper3 activity. In another aspect, the invention provides a method of contraception in which a compound which decreases CatSper3 activity is administered to a male or female subject. In each of the foregoing embodiments, the compound can be in an injection, a transdermal patch, a bioerodable implant, a lubricant, a moisturizer, a foam, a jelly, or a sponge. If the subject is a female, the compound can be administered into at least one of the vagina, uterus or fallopian tubes. In each of the foregoing embodiments, the compound can be a nucleic acid which is antisense to at least a portion of a CatSper3 gene or an antibody to a CatSper3 protein, including an Fab fragment, an $F(ab')_2$ fragment, an Fv fragment, or an scFv fragment. In some embodiments, the subject is a mammal. In some embodiments, the subjects are humans, dogs, cats, cows, sheep, horses, mice, rats, raccoons, and gophers. In others embodiments, the subjects are fish, amphibians or insects. In related aspects, the invention provides for the use of a compound which decreases CatSper3 activity in the preparation of a medicament for decreasing the fertility of a male subject, or causing reversible infertility in a male subject, or in the preparation of a contraceptive for administration to a male or female. thus, the invention provides contraceptive preparations including compounds which decrease CatSper3 activity, including nucleic acids which are antisense to at least a portion of a CatSper3 gene and antibodies to a CatSper3 protein.

In another aspect, the invention provides method of diagnosing a CatSper3-related disorder in a mammal by determining the presence or absence of a mutation in a CatSper3 gene. In some embodiments, the presence or absence of differences between a determined nucleic acid or amino acid sequence and a reference sequence indicates the presence or absence of mutations in the CatSper3 gene. In some embodiments, the method includes contacting at least a fragment of the CatSper3 protein with an antibody known to bind to a CatSper3 protein in which a mutation is known to be present or absent and detecting binding between the antibody and the CatSper3 protein. In other embodiments, the method includes measuring an indicator of CatSper3 activity in a cell; and comparing the measured indicator to a reference level. The indicator can be an indicator of the level of mRNA encoding CatSper3 protein, an indicator of the level of CatSper3 protein, an indicator of cation flux across a membrane of said cell, or an indicator of whole cell or channel currents of said cell. In some embodiments, the disorder is CatSper3-related infertility. In another aspect, the invention provides methods of genotyping a subject with respect to a CatSper3 gene.

In another aspect, the invention provides a method of in vitro fertilization by sperm having decreased CatSper3 activity, decreased motility, or decreased ability to penetrate a zona pellucida, in which a zona pellucida is removed from at least one ovum; and the ovum is contacted with at least one of sperm.

In another aspect, a method of treating a subject characterized by infertility due to decreased CatSper3 activity is provided. The method includes transforming sperm or sperm progenitors of the subject with a genetic construct capable of expressing a CatSper3 protein and using transformed sperm of said subject to fertilize an ovum. Alternatively, the method includes administering a CatSper3 protein to sperm or sperm progenitors of the subject.

In another aspect, the invention provides methods of diagnosing an anti-CatSper3 antibody-mediated infertility caused by anti-CatSper3 antibodies present in a female urogenital tract is provided. In another aspect, methods of treating an anti-CatSper3 antibody-mediated infertility caused by anti-CatSper3 antibodies present in a female urogenital tract are provided.

In another aspect, the invention provides methods of conducting a drug discovery business including (a) identifying, by an assay of the invention, one or more agents which antagonize CatSper3 activity; (b) determining if an agent identified in step (a), or an analog thereof, inhibits at least one of sperm motility or egg penetrance; (c) conducting therapeutic profiling of an agent identified as an inhibitor in step (b) for efficacy and toxicity in one or more animal models; and (d) formulating a pharmaceutical preparation including one or more agents identified in step (c) as having an acceptable therapeutic profile. In some embodiments, the method further includes the step of establishing a system for distributing the pharmaceutical preparation for sale, and optionally including establishing a sales group for marketing the pharmaceutical preparation.

BRIEF DESCRIPTION OF THE DRAWINGS

The following drawings are illustrative of embodiments of the invention and are not meant to limit the scope of the invention.

FIG. 1 shows the primary structure of mouse CatSper3 protein. (a) Amino acid sequence; the 6 putative transmembrane domains and the pore region are underlined.

FIG. 2 shows the primary structure of human CatSper3 protein. (a) Amino acid sequence; the 6 putative transmembrane domains and the pore region are underlined.

FIG. 3 shows cladograms of the (a) murine and (b) human CatSper family.

DETAILED DESCRIPTION

The present invention depends, in part, upon the identification, isolation and characterization of a cation channel protein which is expressed in sperm cells, but not in other tissues tested, and which plays a significant role in the motility of sperm and their ability to fertilize ova. The protein has been designated CatSper3 to indicate that it is the third Cation channel which is Sperm-specific to be identified. Other members of the CatSper family of proteins include CatSper1 (Ren et al. (2001), *Nature* 413:603-9; U.S. Prov. Appln. Ser. No. 60/288,402, filed May 3, 2001; U.S. Prov. Appln. Ser. No. 60/327,167, filed Oct. 4, 2001; PCT Intl. Appln. No. PCT/US02/13487, filed May 3, 2002), CatSper2 (Quill et al. (2001), *Proc. Natl. Acad. Sci.* (*USA*) 98(22): 12527-31; U.S. Prov. Appln. Ser. No. 60/345,324, filed Oct. 22, 2001), and CatSper4 (co-pending U.S. Prov. Appln. 60/402,115, filed of even date herewith). Significantly, inhibition of the activity of CatSper1 has been shown to cause a substantial decrease in the motility of sperm cells, particularly the most vigorous sperm tail beating required for penetration of the zona pellucida (ZP) and subsequent fertilization, and CatSper1 knockout mice have been shown to be infertile. Like CatSper1 and the other members of the CatSper family of proteins, the CatSper3 protein includes six transmembrane domains and a pore region, its expression is strictly localized to testis (e.g., spermatocytes and the principal piece of sperm), and its function appears related to cyclic nucleotide-mediated calcium entry and motility. Data indicate that the CatSper proteins may heteromultimerize to function in vivo.

The CatSper3 gene encodes six transmembrane domains and a pore region. The gene product is exclusively expressed in the testis and not in other tissues such as the heart, brain, spleen, lung, liver, skeletal muscle, or kidney. In sperm, the channel is localized primarily to the tail's principal piece, not the head or midpiece.

Agonists and antagonists of the activity of the CatSper3 protein can modulate sperm motility and, therefore, can be used to treat infertility or as male and female contraceptives.

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference. In particular, the entire disclosures of U.S. Prov. Appln. Ser. No. 60/288,402, filed May 3, 2001, U.S. Prov. Appln. Ser. No. 60/327,167, filed Oct. 4, 2001, U.S. Prov. Appln. Ser. No. 60/345,324, filed Oct. 22, 2001, and PCT Intl. Appln. No. PCT/US02/13487, filed May 3, 2002, are incorporated herein by reference.

DEFINITIONS

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent techniques which would be apparent to one of skill in the art. In order to more clearly and concisely describe the subject matter which is the invention, the following definitions are provided for certain terms which are used in the specification.

As used herein, the term "CatSper3 protein" means a sperm-specific cation channel such as the human CatSper3 protein disclosed in SEQ ID NO: 2, human allelic variants of the disclosed CatSper3 protein, mammalian homologs of these human CatSper3 proteins, and functional equivalents thereof. The term CatSper3 protein refers to naturally occurring proteins as isolated from sperm, recombinantly produced proteins from cells transformed with CatSper3 genes, and fusion proteins in which CatSper3 sequences are fused to N-terminal or C-terminal polypeptides. The term "fragment" refers to fragments of the CatSper3 proteins, such as structural domains and epitopes. A fragment of a CatSper3 protein comprises at least six amino acid residues.

As used herein, the term "CatSper3 gene" means a gene encoding a CatSper3 protein, including the human CatSper3 protein disclosed in SEQ ID NO: 2, human allelic variants of the disclosed CatSper3 protein, mammalian homologs of these human CatSper3 proteins, and functional equivalents thereof. The term CatSper3 gene refers to both naturally occurring genes as isolated from genomic DNA, and recombinantly produced genes in which the CatSper3 coding regions are operably joined to either endogenous or exogenous regulatory elements, with or without intron sequences, and with or without 5' or 3'-flanking sequences which can encode heterologous (i.e., non-CatSper3) sequences to form a CatSper3 fusion protein. A CatSper3 gene will include, at a minimum, a coding region encoding the protein operably joined to regulatory elements (e.g., promoters, enhancer) which allow transcription of the coding region to mRNA which can be translated into a CatSper3 protein.

As used herein "CatSper3" activity means any normal biological activity of a wild-type CatSper3 protein when expressed in a cell or cell type in which CatSper3 is normally expressed and under conditions under which CatSper3 is normally expressed. Such activity can include induction of an ion current; mediation of cAMP-induced $Ca^{2+}$ influx; restoration of sperm motility when expressed in CatSper3−/− sperm; and/or restoration of the ability to penetrate eggs when expressed in CatSper3−/− sperm. CatSper3 activity can be measured in sperm cells or spermatocytes, or in other cells in which any necessary accessory factors are present.

As used herein with respect to nucleic acid and amino acid sequences, the term "identity" means a measure of the degree of similarity of two sequences based upon an alignment of the sequences which maximizes identity and which is a function of the number of identical nucleotides or residues, the number of total nucleotides or residues, and the presence and length of gaps in the sequence alignment. A variety of algorithms and computer programs are available for determining sequence identity using standard parameters. For example, Gapped BLAST or PSI-BLAST (Altschul et al. (1997), Nucleic Acids Res. 25:33 89-3402), BLAST (Altschul et al. (1990) *J. Mol. Biol.* 215:403-410), and Smith-Waterman (Smith et al. (1981), *J. Mol. Biol.* 147:195-197). As used herein, percent identity is based upon the default values for the BLAST algorithms.

As used herein, the term "homolog" means a protein which is evolutionarily-related to and shares substantial, conserved structural and functional similarity with a reference protein, but which is present in a different species (e.g., human, rat, and insect CatSper3 proteins are homologs of each other).

As used herein, the term "mutation" refers to a change in a nucleic acid sequence, whether or not expressed as a change in a corresponding encoded protein sequence, relative to some reference sequence. The reference sequence can be a "wild-type" sequence (i.e., one or more high frequency sequences in a population corresponding to a "normal" phenotype), or any other sequence. As used herein, the term mutation is intended to be synonymous with the term polymorphism, and therefore the differences between any two non-identical sequences can be regarded as mutations. The term mutation is intended to encompass insertions, deletions and/or substitutions of one or more nucleotides relative to a reference sequence.

As used herein, the terms "exogenous" or "heterologous" mean, with respect to two or more genetic sequences, that the genetic sequences do not occur in the same physical relation to each other in nature and/or do not naturally occur within the same genome. For example, a genetic construct can include a coding region which is operably joined to one or more regulatory elements, and these sequences are considered heterologous to each other if they are not operably joined in nature and/or they are not found in the same genome in nature. Similarly, a genetic construct which is introduced into a cell is considered heterologous to that cell to the extent that it contains genetic sequences not found in that cell. In addition, a synthetically-produced genetic sequence based upon a naturally occurring sequence, will be heterologous to the naturally-occurring sequence to the extent codons have been altered and the synthetic sequence does not exist in nature. Allelic variants of a sequence in a species are not considered heterologous to each other.

As used herein, the term "operably joined" refers to a covalent and functional linkage of genetic regulatory elements and a genetic coding region which can cause the coding region to be transcribed into mRNA by an RNA polymerase which can bind to one or more of the regulatory elements. Thus, a regulatory region, including regulatory elements, is operably joined to a coding region when RNA polymerase is capable under permissive conditions of binding to a promoter within the regulatory region and causing transcription of the coding region into mRNA. In this context, permissive conditions would include standard intracellular conditions for constitutive promoters, standard conditions and the absence of a repressor or the presence of an inducer for repressible/inducible promoters, and appropriate in vitro conditions, as known in the art, for in vitro transcription systems.

As used herein, the term "expression" refers to the process by which a coding sequence of a gene is transcribed into a primary mRNA transcript, the primary mRNA transcript is processed into a mature mRNA, and the mature mRNA is translated into a protein. Expression can optionally include post-translation modifications of the resulting polypeptide.

As used herein, the phrase "genetic construct encoding a CatSper3 protein" means a recombinant DNA, RNA, or nucleic acid analog molecule which includes a genetic sequence encoding, or which is complementary to a genetic sequence encoding, the amino acid sequence of the CatSper3 protein, and which is capable of being expressed in a cell which has been transformed with the construct. The construct can express the CatSper3 protein transiently, or can stably integrate into the genome of the cell and express the protein conditionally or constitutively.

As used herein, the term "vector" means any genetic construct, such as a plasmid, phage, transposon, cosmid, chromosome, virus, virion, etc., which is capable transferring gene sequences between cells. Vectors can be capable of one or more of replication, expression, and insertion or integration, but need not possess each of these capabilities. Thus, the term includes cloning, expression, homologous recombination, and knock-out vectors.

As used herein, with respect to genetic engineering, the term "transform" means to introduce into a cell or an organism an exogenous nucleic acid or nucleic acid analog which replicates within that cell or organism, that encodes a polypeptide sequence which is expressed in that cell or organism, and/or that is integrated into the genome of that cell or organism so as to affect the expression of a genetic locus. The term "transform" is used to embrace all of the various methods of introducing such nucleic acids or nucleic acid analogs, including, but not limited to the methods referred to in the art as transformation, transfection, transduction, electroporation, ballistic injection, and the like.

As used herein, a "nucleic acid analog" means a molecule having sufficient structural and functional similarity to a nucleic acid to direct sequence-specific forward or reverse transcription of complementary nucleic acids, or to direct sequence-specific translation of an encoded polypeptide within a living cell.

As used herein, the term "reporter gene" means any genetic sequence which, when expressed, has a biochemical or phenotypic effect which is detectable. Reporter genes are also known in the art as "marker" genes.

As used herein, the term "antibody" is intended to embrace naturally produced antibodies, recombinantly produced antibodies, and antibody fragments such as Fab fragments, F(ab')2 fragments, Fv fragments, and single-chain Fv fragment (scFv).

As used herein, the term "effective amount" of an agonist or antagonist, or an enhancer or repressor, means the total amount of the active component(s) of a composition that is sufficient to cause a statistically significant change on a detectable biochemical or phenotypic characteristic. When applied to an individual active ingredient, administered alone, the term refers to that ingredient alone. When applied to a combination, the term refers to combined amounts of the active ingredients that result in the effect, whether administered in combination, serially or simultaneously.

As used herein, the term "substantially pure" means a preparation which contains at least 60% (by dry weight) of the protein of interest, exclusive of the weight of other intentionally included compounds. Preferably the preparation is at least 75%, more preferably at least 90%, and most preferably at least 99%, by dry weight of the protein of interest, exclusive of the weight of other intentionally included compounds. Purity can be measured by any appropriate method, e.g., column chromatography, gel electrophoresis, amino acid compositional analysis or HPLC analysis. If a preparation intentionally includes two or more different proteins of the invention, a "substantially pure" preparation means a preparation in which the total dry weight of the protein of the invention is at least 60% of the total dry weight, exclusive of the weight of other intentionally included compounds. Preferably, for such preparations containing two or more proteins of the invention, the total weight of the proteins of the invention should be at least 75%, more preferably at least 90%, and most preferably at least 99%, of the total dry weight of the preparation, exclusive of the weight of other intentionally included compounds. Thus, if the proteins of the invention are mixed with one or more other compounds (e.g., diluents, detergents, excipients, salts, sugars, lipids) for purposes of administration, stability, storage, and the like, the weight of such other compounds is ignored in the calculation of the purity of the preparation.

As used herein, the term "contacted" as in the phrase "A is contacted with B," means that A and B are brought into sufficient physical proximity to interact at the molecular level, as by mixing A and B together in a solution, or pouring a solution of A over B on substrate. As used herein, the phrase "A is contacted with B" is intended to be equivalent to "B is contacted with A" and is not intended to imply that either element is fixed relative to the other, or that either element is moved relative to the other.

As used herein, the terms "modulate" or "affect" mean to either increase or decrease. As used herein, the terms "increase" and "decrease" mean, respectively, statistically significantly increase (i.e., $p<0.1$) and statistically significantly decrease (i.e., $p<0.1$).

General Considerations.

The present invention depends, in part, upon the identification, isolation and characterization of a cation channel protein which is expressed in sperm cells, but not in other tissues tested, and which plays a significant role in the motility of sperm and their ability to fertilize ova. The protein has been designated CatSper3 to indicate that it is the third Cation channel which is Sperm-specific to be identified.

The CatSper3 gene encodes six transmembrane domains and a pore region. The gene product is exclusively expressed in the testis and not in other tissues such as the heart, brain, spleen, lung, liver, skeletal muscle, or kidney. In sperm, the channel is localized primarily to the tail's principal piece, not the head or midpiece.

Agonists and antagonists of the activity of the CatSper3 protein can modulate sperm motility and, therefore, can be used to treat infertility or as male and female contraceptives.

In particular, CatSper3 represents an excellent target for non-hormonal contraceptives for both males and females, including humans and other mammals. Identification of the CatSper3 gene and protein also presents new targets for the diagnosis and treatment of infertility, and thus provides for new assays for the identification of compounds that can modulate fertility.

CatSper3 Nucleic Acids.

In one aspect, the present invention provides nucleic acid molecules, or nucleic acid analogs, encoding the CatSper3 proteins, or useful fragments thereof. The full length cDNA of the human CatSper3 gene is disclosed as SEQ ID NO: 1. The full-length cDNA sequence of a murine homolog is disclosed as SEQ ID NO: 3. The 5' regulatory region of a human allele, including 2079 bases extending 5' from the translational start codon, is disclosed as SEQ ID NO: 5. The 5' untranslated region of this human allele is disclosed as SEQ ID NO: 6. The 3' untranslated region of this human allele, including 478 bases extending 3' from the translational termination codon, is disclosed as SEQ ID NO: 7.

Nucleic acid molecules of the invention can be DNA or RNA molecules, or hybrid DNA-RNA molecules. The nucleic acid analogs of the invention can be any of those known in the art, such as peptide nucleic acids, analogs including modified bases (e.g., 2'-halogeno-2'-dexynucleosides) and/or analogs including modified internucleoside linkages (e.g., phosphorothioate linkages), which are useful in applications such as in vitro translation or antisense technologies. In the remainder of this disclosure and the appended claims, whenever the term "nucleic acids" is used, the term is intended to embrace nucleic acid analogs when such analogs would be useful or suitable in the context of the usage. The nucleic acids can be sense molecules corresponding to all or a portion of a CatSper3 gene sequence, or can be antisense molecules which are complementary to all or a portion of a CatSper3 gene sequence. The nucleic acids can be derived from or correspond to genomic DNA or cDNA, or can be synthetic molecules based upon a CatSper3 protein sequence and the genetic code (e.g., synthetic nucleic acids which reflect the codon usage preferences in the host cells used in an expression systems).

In some embodiments, the CatSper3 nucleic acids comprise the entire coding region of a CatSper3 gene (e.g., SEQ ID NO: 1 or SEQ ID NO: 3). Such nucleic acids can be used to produce genetic constructs for transformation of cells, or for in vitro transcription and translation systems. Such nucleic acids can also be used as probes in hybridization assays to detect CatSper3 sequences in samples of other nucleic acids.

In other embodiments, subsets of the CatSper3 nucleic acid sequences are provided for use as primers for nucleic acid amplification reactions, as probes in hybridization assays to detect CatSper3 sequences in samples of other nucleic acids, or as probes to distinguish normal or wild-type sequence from abnormal or mutant sequences. In these embodiments, the nucleic acids of the invention comprise at 10, preferably at least 12, more preferably at least 14 and most preferably at least 16 consecutive nucleotides selected from a CatSper3 sequence such as SEQ ID NO: 1. Depending upon the nature of the application, it may be preferable to choose CatSper3 sequences which will have unique targets, or which are expected to have unique targets, within a sample being probed or amplified. Thus, for example, sequences which are longer and sequences which do not include frequently repeated elements (for example, polyadenylation signals) are more likely to be uniquely represented within any given sample. For purposes of choosing primers for amplification reactions, sequences of at least 15, and preferably 18-25 nucleotides are preferred.

In certain preferred embodiments, nucleic acids are provided which encode structural domains of a CatSper3 protein, or which encode fragments of the protein which can serve as epitopes for the generation of antibodies. Thus, for example, preferred nucleic acids include those encoding the transmembrane domains of the CatSper3 proteins (i.e., approximately residues 88-117, 128-152, 155-180, 217-242, 245-268 and 282-308 of SEQ ID NO: 2, approximately residues 64-95, 101-129, 131-178, 191-218, 221-246 and 259-284 of SEQ ID NO: 4, and allelic variants and homologs thereof), encoding the extracellular loops between transmembrane domains (i.e., approximately residues 118-127, 181-216 and 269-281 of SEQ ID NO: 2, approximately residues 96-100, 179-190 and 247-258 of SEQ ID NO: 4, and allelic variants and homologs thereof), or encoding the pore region (i.e., approximately residues 257-265 of SEQ ID NO: 2, approximately residues 234-241 of SEQ ID NO: 4, and allelic variants and homologs thereof). Other preferred nucleic acid acids include those encoding epitopes of the CatSper3 proteins having high predicted antigenicity, as identified by standard sequence analysis techniques described below. Thus, for example, preferred nucleic acids include those encoding sequences within a high predicted antigenicity epitope of SEQ ID NO: 2, or within a high predicted antigenicity epitope (e.g., residues 386-407) of SEQ ID NO: 4, and allelic and mammalian homologs thereof.

In certain embodiments, nucleic acids are provided which encode polypeptides have at least 80%, and preferably at least 85%, 90% or 95% amino acid sequence identity with at least a structural domain of a CatSper3 protein. Thus, in some embodiments, a nucleic acid is provided which encodes a polypeptide having at least 80%, 85%, 90% or 95% amino acid sequence identity with a transmembrane domain of a CatSper3 proteins (e.g., approximately residues 88-117, 128-152, 155-180, 217-242, 245-268 and 282-308 of SEQ ID NO: 2, approximately residues 64-95, 101-129, 131-178, 191-218, 221-246 and 259-284 of SEQ ID NO: 4, and allelic variants and homologs thereof), an extracellular loop between transmembrane domains (e.g., approximately residues 118-127, 181-216 and 269-281 of SEQ ID NO: 2, approximately residues 96-100, 179-190 and 247-258 of SEQ ID NO: 4, and allelic variants and homologs thereof), or a pore region (e.g., approximately residues 257-265 of SEQ ID NO: 2, approximately residues 234-241 of SEQ ID NO: 4, and allelic variants and homologs thereof). In some preferred embodiments, nucleic acids are provided encoding a polypeptide having at least 80%, 85%, 90% or 95% amino acid sequence identity with a CatSper3 protein and having CatSper3 activity. The ability of a protein to exhibit CatSper3 activity can be measured by its ability to complement a CatSper3−/− mutant (e.g., a CatSper3 knock-out mutant) and restore a normal or CatSper3+/+ phenotype (e.g., to restore sperm motility) in a cell otherwise capable of expressing CatSper3 activity (e.g., a sperm cell from the CatSper3−/− mutant).

In other embodiments, isolated nucleic acids are provided which include a nucleotide sequence that hybridizes to at least a portion of a CatSper3 coding sequence (e.g., SEQ ID NO: 1 or SEQ ID NO: 3) under stringent hybridization conditions. Such conditions include hybridizations employing a wash step of 1.0×SSC at 65° C., and equivalents thereof. More stringent conditions can include wash steps of 0.5×SSC, 0.2× SSC, or even 0.1×SSC. Other equivalently stringent conditions are well known in the art. See, e.g., Ausubel et al., eds.

(1989), Current Protocols in Molecular Biology, Vol. I, John Wiley & Sons, Inc., New York. In preferred embodiments, the nucleic acid encodes a polypeptide having CatSper3 activity.

In another aspect, the invention provides nucleic acids, either isolated or existing within cells, in which a nucleotide sequence encoding a polypeptide having CatSper3 activity is operably joined to a heterologous regulatory region such that the CatSper3 sequence is expressed. Thus, in certain embodiments, a heterologous regulatory region can be inserted into a chromosome such that it is operably joined to an endogenous CatSper3 sequence. In some embodiments, the polypeptide has at least 80%, 85%, 90% or 95% amino acid sequence identity with an amino acid sequence of SEQ ID NO: 2 or 4. In other embodiments, the nucleic acid encoding the polypeptide hybridizes to at least a portion of a nucleic acid of SEQ ID NO: 1 or SEQ ID NO: 3 under conditions including a wash step of 1.0×SSC at 65° C., 0.5×SSC, 0.2×SSC, or 0.1×SSC.

In certain embodiments, the nucleic acids of the invention encode polypeptides including a CatSper3 sequence of at least 50 amino acid residues in length, and preferably at least 100, 200 or 300 amino acid residues in length. These polypeptides can include a CatSper3 sequence which includes at least one transmembrane domain, at least one extracellular loop domain, at least a pore region, or combinations thereof. In some preferred embodiments, the polypeptide has CatSper3 activity. Such activity can include induction of ion current; mediation of cAMP-induced $Ca^{2+}$ influx; restoration of sperm motility when expressed in CatSper3−/− sperm; and/or restoration of the ability to penetrate eggs when expressed in CatSper3−/− sperm.

In another aspect, the invention provides kits for detecting at least a portion of a CatSper3 nucleic acid (i.e., CatSper3 genomic DNA, mRNA, cDNA or amplification products thereof). The kits include an isolated nucleic acid of the invention as a probe and means for detecting the probe. The means for detecting the probe can be a detectable label bound to the probe or a secondary nucleic acid probe for detecting the first probe (e.g., labeled secondary nucleic acid which specifically hybridizes to the isolated nucleic acid.).

Genetic Constructs.

In another aspect, the present invention provides genetic constructs comprising sequences selected from CatSper3 genes. In certain embodiments, the CatSper3 gene sequences are selected from the coding region of the CatSper3 gene, and in other embodiments, the CatSper3 gene sequences can be chosen from the CatSper3 regulatory regions extending approximately 500-1,500 bases, or approximately 600-1,000 bases, 5' of the start codon, and approximately 250-1,000 bases, or approximately 500-750 bases, 3' of the termination codon.

In one series of embodiments, CatSper3 coding sequences (e.g., the entire coding region, sequences encoding structural domains, sequences encoding potential epitopes, or sequences encoding useful primers or probes) are operably joined to an endogenous or exogenous regulatory region to form an expression construct. Useful regulatory regions for these purposes include the endogenous CatSper3 regulatory region, constitutive promoter sequences (e.g., CMV, SV40, EF2), inducible promoter sequences (e.g., lacZ, tet). Many useful vector systems are now widely available. For example, useful bacterial vectors include, but are not limited to, pQE70, pQE60, pQE-9 (Qiagen, Valencia, Calif.), pBluescript II (Stratagene, La Jolla, Calif.), and pTRC99a, pKK223-3, pDR540 and pRIT2T (Pharmacia, Piscataway, N.J.), pTrc (Amann et al. (1988), *Gene* 69:301-315) and pET 11d (Studier et al. (1990), *Methods in Enzymol.* 185:60-89). Examples of vectors for expression in yeast include pYepSec1 (Baldari et al. (1987), *EMBO J.* 6:229-234), pMFa (Kurjan et al. (1982), *Cell* 30:933-943), pJRY88 (Schultz et al. (1987), *Gene* 54:113-123), and pYES2 (Invitrogen Corporation, San Diego, Calif.). The CatSper3 proteins can also be expressed in insect cells (e.g., Sf 9 cells) using, for example, baculovirus expression vectors including, but not limited to, pAc vectors (Smith et al. (1983), *Mol. Cell Biol.* 3:2156-2165) and pVL vectors (Lucklow et al. (1989), *Virology* 170:31-39). Examples of mammalian expression vectors include, but are not limited to, pCDM8 (Seed (1987), *Nature* 329:840) and pMT2PC (Kaufman et al. (1987), *EMBO J.* 6:187-195). Other useful eukaryotic vectors include, but are not limited to, pXT1, pSG5 (Stratagene, La Jolla, Calif.), and pSVK3, pBPV, pMSG, and PSVLSV40 (Pharmacia, Piscataway, N.J.). Thus, one of ordinary skill in the art can choose a vector system appropriate to the host cell to be transformed.

In other embodiments, the vectors comprise defective or partial CatSper3 sequences in a "knock-out" vector. Such vectors are well-known in the art and can be used to produce a transgenic organism in which an endogenous gene is "knocked-out" by recombination with a partially homologous exogenous sequence which introduces a mutation within the endogenous sequence. Typically, the vector is directed at an endogenous target sequences which can be all or part of a gene of interest. The vector includes 5' and 3' flanking sequences which are homologous to the 5' and 3' ends of the target. Between the 5' and 3' flanking sequences is the sequence including the mutation. The mutation can be a termination mutation, frame-shift mutation, large deletion, or even the introduction of a new coding sequence which serves both to disrupt the endogenous gene and to act as a marker for successful homologous recombination. Knock-out vectors are further discussed below.

In other embodiments, the CatSper3 coding sequences can be joined to regulatory regions and heterologous coding sequences to form a genetic construct or fusion vector which encodes a fusion protein. Fusion vectors and fusion proteins can be useful to increase the expression of the CatSper3 protein, to increase the solubility of the CatSper3 protein, and aid in the purification of the CatSper3 protein (e.g., by acting as a ligand for affinity purification). A proteolytic cleavage site can be introduced at the junction of the CatSper3 and non-CatSper3 protein sequences so that the CatSper3 protein can easily be separated from the fusion moiety. Typical fusion expression vectors include pGEX (Smith et al. (1988), *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In another series of embodiments, vectors or genetic constructs are produced in which the coding region from a reporter gene is operably joined to the regulatory region of a CatSper3 gene (e.g., SEQ ID NO: 5 and, optionally, SEQ ID NO: 6 at the 5' end and, optionally, SEQ ID NO: 7 at the 3' end). Such genetic constructs are useful in assays to identify or characterize compounds that enhance or repress CatSper3 gene expression by enhancing or repressing transcription of the CatSper3 gene. A wide variety of suitable reporter genes are known to those of skill in the art, and are commercially available. Examples include, but are not limited to, the lacZ and luciferase genes.

Useful CatSper3 regulatory elements include sequences having at least 80% nucleotide identity to at least 100 consecutive nucleotides selected from SEQ ID NO: 5, preferably at least 200 consecutive nucleotides, and more preferably at least 300-500 consecutive nucleotides. Useful regulatory elements will retain the ability to promote transcription of a coding sequence operably joined to the element in a mammalian cell in which a CatSper3 gene is expressed. In particular, useful regulatory elements will retain the ability to promote transcription in cells in which the CatSper3 gene from which the element was derived is expressed, or in which a homolog of that CatSper3 gene is expressed.

Transformed Cell Lines.

In another aspect, the present invention provides cell lines transformed with the nucleic acid molecules of the invention. Such cell lines can simply propagate these nucleic acids (e.g., when transformed with cloning vectors) or can express the polypeptides encoded by these nucleic acids (e.g., when transformed with expression vectors). Such transformed cell lines can be used to produce the CatSper3 proteins and CatSper3 fragments of the invention, or can be used in assays to screen for compounds that enhance, repress, agonize, or antagonize CatSper3 expression or activity.

The transformed cells can be produced by introducing into a cell an exogenous nucleic acid or nucleic acid analog which replicates within that cell, that encodes a polypeptide sequence which is expressed in that cell, and/or that is integrated into the genome of that cell so as to affect the expression of a genetic locus. The transformation can be achieved by any of the standard methods referred to in the art as transformation, transfection, transduction, electroporation, ballistic injection, and the like. The method of transformation is chosen to be suitable to the type of cells being transformed and the nature of the genetic construct being introduced into the cells.

Preferred cell lines for transformation include bacterial cells (e.g., *Escherichia coli*), yeast cells (e.g., *Saccharomyces cerevisiae*), insect cells (e.g., *Drosophila melanogaster* Schneider cells), nematode cells (e.g., *Caenorhabditis elegans*), amphibian cells (e.g., *Xenopus* oocytes), rodent cells (e.g., *Mus musculus* (e.g., murine 3T3 fibroblasts), *Rattus rattus*, Chinese Hamster Ovary cells (e.g., CHO-K1)), and human cells (e.g., human skin fibroblasts, human embryonic kidney cells (e.g., HEK-293 cells), COS cells, spermatogonial cells). Transformed mammalian cells useful in the invention include somatic cells, fetal cells, embryonic stem cells, zygotes, gametes, germ line cells and transgenic animal cells.

Appropriate cells can be transformed with any of the above-described genetic constructs in order to produce CatSper3 proteins, including fragments of CatSper3 proteins, fusion proteins of CatSper3 proteins, or marker proteins under the control of a CatSper3 regulatory region.

The cells can be transformed according to any method known in the art appropriate to the cell type being transformed. Appropriate methods can include those described generally in, e.g., Sambrook et al. (1989), *Molecular Cloning: A Laboratory Manual*, Cold Spring Harbor Laboratories, New York; and Davis et al. (1986), *Basic Methods in Molecular Biology*, Elsevier. Particular methods include calcium phosphate co-precipitation (Graham et al. (1973), *Virol.* 52:456-467), direct micro-injection into cultured cells (Capecchi (1980), *Cell* 22:479-488), electroporation (Shigekawa et al. (1988), *BioTechniques* 6:742-751), liposome-mediated gene transfer (Mannino et al. (1988), *BioTechniques* 6:682-690), lipid-mediated transduction (Felgner et al. (1987), *Proc. Natl. Acad. Sci. USA* 84:7413-7417), and nucleic acid delivery using high-velocity microprojectiles (Klein et al. (1987), *Nature* 327:70-73).

Transgenic Animals.

The present invention also provides for the production of transgenic non-human animal models in which wild type, allelic variant, chimeric, or antisense CatSper3 sequences are expressed, or in which CatSper3 sequences have been inactivated or deleted (e.g., "knock-out" constructs) or replaced with reporter or marker genes (e.g., "knock-in reporter" constructs). The CatSper3 sequences can be conspecific to the transgenic animal (e.g., murine sequences in a transgenic mouse) or transpecific to the transgenic animal (e.g. human sequence in a transgenic mouse). In such a transgenic animal, the transgenic sequences can be expressed inducibly, constitutively or ectopically. Expression can be tissue-specific or organism-wide. Engineered expression of CatSper3 sequences in tissues and cells not normally containing CatSper3 gene products can cause novel alterations of cation flux and lead to novel cell or tissue phenotypes. Ectopic or altered levels of expression of CatSper3 sequences can alter cell, tissue and/or developmental phenotypes. Transgenic animals are useful as models of disorders arising from defects in CatSper3 activity.

Transgenic animals are also useful for screening compounds for their effects on CatSper3 activity. Transgenic animals transformed with reporter constructs can be used to measure the transcriptional effects of small molecules or drugs or physical perturbations on the expression of CatSper3 genes and proteins in vivo. The transgenic animals of the invention, can be used to screen such compounds for therapeutic utility.

Animal species suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) are preferred due to their relative ease of maintenance and shorter life spans. Transgenic non-human primates may be preferred for longer term studies due to their greater similarity to humans.

Using the nucleic acids disclosed and otherwise enabled herein, there are several available approaches for the creation of a transgenic animal. Thus, the enabled animal models include: (1) animals in which sequences encoding at least a functional fragment of a CatSper3 gene has been recombinantly introduced into the genome of the animal as an additional gene, under the regulation of either an exogenous or an endogenous promoter element, and as either a minigene (i.e., a genetic construct of the CatSper3 gene based on cDNA with introns removed) or a large genomic fragment; (2) animals in which sequences encoding at least a functional fragment of a CatSper3 gene have been recombinantly substituted for one or both copies of the animal's endogenous CatSper3 gene by homologous recombination or gene targeting; (3) animals in which one or both copies of one of the animal's homologous CatSper3 genes have been recombinantly "humanized" by the partial substitution of sequences encoding the human homolog by homologous recombination or gene targeting; (4) animals in which sequences encoding a reporter gene have replaced the endogenous CatSper3 gene by homologous recombination; (5) and "knock-out" animals in which one or both copies of the animal's CatSper3 sequences have been partially or completely inactivated by the insertion, deletion or substitution of one or more nucleotides by homologous recombination. These and other transgenic animals of the invention are useful as models of infertility or other disorders arising from defects in the CatSper3 gene and/or protein. These animals are also useful for screening compounds for their effects on the CatSper3 gene and/or protein.

To produce an animal model (e.g., a transgenic mouse), a wild type or allelic variant CatSper3 sequence or a wild type or allelic variant of a recombinant nucleic acid encoding at least a functional fragment of a CatSper3 protein is preferably inserted into a germ line or stem cell using standard techniques of oocyte or embryonic stem cell microinjection, or other form of transformation of such cells. Alternatively, other cells from an adult organism can be employed. Animals produced by these or similar processes are referred to as transgenic. Similarly, if it is desired to inactivate or replace an endogenous CatSper3 sequence, homologous recombination using oocytes, embryonic stem or other cells can be employed. Animals produced by these or similar processes are referred to as "knock-out" (inactivation) or "knock-in" (replacement) models.

For oocyte injection, one or more copies of the recombinant DNA constructs of the present invention can be inserted into the pronucleus of a just-fertilized oocyte. This oocyte is then reimplanted into a pseudo-pregnant foster mother. The live born animals are screened for integrants using standard DNA/mRNA analysis (e.g., from the tail veins of offspring mice) for the presence of the inserted recombinant transgene sequences. The transgene can be either a complete genomic sequence introduced into a host as part of a yeast artificial chromosome (YAC), bacterial artificial chromosome (BAC), or other chromosome DNA fragment; as a cDNA with either the endogenous promoter or a heterologous promoter; or as a minigene containing all of the coding regions and other elements found to be necessary for optimum expression.

To create a transgene, the target sequence of interest (e.g., a wild type or allelic variant of a CatSper3 sequence) is typically ligated into a cloning site located downstream of a promoter element which will regulate the expression of RNA from the sequence. Downstream of the coding sequence, there is typically a polyadenylation sequence. An alternative approach to creating a transgene is to use an exogenous promoter and regulatory sequences to drive expression of the transgene. Finally, it is possible to create transgenes using large genomic DNA fragments such as YACs which contain the entire desired gene as well as its appropriate regulatory sequences.

Animal models can be created by targeting endogenous CatSper3 sequences for homologous recombination. These targeting events can have the effect of removing endogenous sequence (knock-out) or altering the endogenous sequence to create an amino acid change associated with human disease or an otherwise abnormal sequence (e.g., a sequence which is more like the human sequence than the original animal sequence) (knock-in animal models). A large number of vectors are available to accomplish this and appropriate sources of genomic DNA for mouse and other animal genomes to be targeted are commercially available (e.g., GenomeSystems Inc., St. Louis, Mo.).

The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out.

Retroviral infection of early embryos can also be done to insert the recombinant DNA constructs of the invention. In this method, the transgene (e.g., a wild type or allelic variant of a CatSper3 sequence) is inserted into a retroviral vector which is used to directly infect embryos (e.g., mouse or non-human primate embryos) during the early stages of development to generate partially transgenic animals, some of which bear the transgenes in germ line cells.

Alternatively, homologous recombination using a population of stem cells allows for the screening of the population for successful transformants. Once identified, these can be injected into blastocysts, and a proportion of the resulting animals will show germ line transmission of the transgene.

Techniques of generating transgenic animals, as well as techniques for homologous recombination or gene targeting, are now widely accepted and practiced. A laboratory manual on the manipulation of the mouse embryo, for example, is available which details standard laboratory techniques for the production of transgenic mice (Hogan, et al. (1986), Manipulating the Mouse Embryo, Cold Spring Harbor Laboratory Press, Cold Spring Harbor, N.Y.).

CatSper3 Proteins and Polypeptides.

In another aspect, the present invention provides substantially pure preparations of CatSper3 proteins. The proteins can be isolated from sperm cells, using standard techniques such as immunoaffinity purification with the antibodies of the invention (see below), but are preferably isolated from the transformed cells of the invention, in which they can be expressed at higher levels and, optionally, as fusion proteins which are more easily isolated and/or purified.

In some embodiments, the CatSper3 proteins comprise the entire translated sequence of the CatSper3 coding region. Examples of such full-length CatSper3 proteins include the human CatSper3 protein disclosed as SEQ ID NO: 2 and the murine homolog disclosed as SEQ ID NO: 4, as well as other CatSper3 proteins, including allelic and mammalian homologs of these human CatSper3 proteins, and functional equivalents thereof.

In other embodiments, the CatSper3 proteins are CatSper3 fragments. Such fragments include the structural domains of the CatSper3 proteins, including the transmembrane, loop and pore-forming regions of the proteins. Preferred structural domains include the transmembrane domains of the human CatSper3 protein (i.e., approximately residues 88-117, 128-152, 155-180, 217-242, 245-268 and 282-308 of SEQ ID NO: 2, approximately residues 64-95, 101-129, 131-178, 191-218, 221-246 and 259-284 of SEQ ID NO: 4, the extracellular loops between transmembrane domains (i.e., approximately residues 118-127, 181-216 and 269-281 of SEQ ID NO: 2, approximately residues 96-100, 179-190 and 247-258 of SEQ ID NO: 4), and the pore region (i.e., approximately residues 257-265 of SEQ ID NO: 2, approximately residues 234-241 of SEQ ID NO: 4), as well as allelic variants and homologs thereof. Other CatSper3 fragments include potentially useful epitopes of the CatSper3 proteins, as identified by standard sequence analysis techniques described below. Thus, for example, preferred CatSper3 fragments include human CatSper3 sequences within a high predicted antigenicity epitope of SEQ ID NO: 2, or within a high predicted antigenicity epitope (e.g., residues 386-407) of SEQ ID NO: 4, and allelic and mammalian homologs thereof.

In certain embodiments, polypeptides are provided having at least 80%, and preferably at least 85%, 90% or 95% amino acid sequence identity with at least a structural domain of a CatSper3 protein. Thus, in some embodiments, a polypeptide is provided having at least 80%, 85%, 90% or 95% amino acid sequence identity with a transmembrane domain of a CatSper3 proteins (e.g., approximately residues 88-117, 128-152, 155-180, 217-242, 245-268 and 282-308 of SEQ ID NO: 2, approximately residues 64-95, 101-129, 131-178, 191-

218, 221-246 and 259-284 of SEQ ID NO: 4, and allelic variants and homologs thereof), an extracellular loop between transmembrane domains (e.g., approximately residues 118-127, 181-216 and 269-281 of SEQ ID NO: 2, approximately residues 96-100, 179-190 and 247-258 of SEQ ID NO: 4, and allelic variants and homologs thereof), or a pore region (e.g., approximately residues 257-265 of SEQ ID NO: 2, approximately residues 234-241 of SEQ ID NO: 4, and allelic variants and homologs thereof). In some preferred embodiments, polypeptides are provided having at least 80%, 85%, 90% or 95% amino acid sequence identity with a CatSper3 protein and having CatSper3 activity. The ability of a protein to exhibit CatSper3 activity can be measured by its ability to complement a CatSper3−/− mutant (e.g., a CatSper3 knock-out mutant) and restore a normal or CatSper3+/+ phenotype (e.g., to restore sperm motility) in a cell otherwise capable of expressing CatSper3 activity (e.g., a sperm cell from the CatSper3−/− mutant).

In certain embodiments, the polypeptides of the invention include a CatSper3 sequence of at least 50 amino acid residues in length, and preferably at least 100, 200 or 300 amino acid residues in length. These polypeptides can include a CatSper3 sequence which includes at least one transmembrane domain, at least one extracellular loop domain, at least a pore region, or combinations thereof. In some preferred embodiments, the polypeptide has CatSper3 activity. Such activity can include induction of ion current when expressed in a cell (e.g., an oocyte); mediation of cAMP-induced $Ca^{2+}$ influx; restoration of sperm motility when expressed in CatSper3−/− sperm; and/or restoration of the ability to penetrate eggs when expressed in CatSper3−/− sperm.

Antibodies Against CatSper3 Proteins and Polypeptides.

In another aspect, the present invention provides substantially pure preparations of antibodies against the CatSper3 proteins, and methods of making such antibodies. In particular, the invention provides antibodies raised against CatSper3 epitopes having high predicted antigenicity, which therefore will selectively bind to and, thereby, isolate or identify wild type and/or variant forms of the CatSper3 proteins.

The antibodies can be raised against the full-length CatSper3 proteins, against fragments of the CatSper3 proteins, or using any CatSper3 epitope which is characteristic of the proteins and which substantially distinguishes them from other proteins. In preferred embodiments, the epitope is a protein sequence of at least 6-12, preferably 10-20, more preferably 15-30 consecutive amino acid residues of a CatSper3 protein. In particular embodiments, the antibodies are raised against CatSper3 epitopes selected from sequences within a high predicted antigenicity epitope of SEQ ID NO: 2, or within a high predicted antigenicity epitope (e.g., residues 386-407) of SEQ ID NO: 4. Other preferred epitopes include allelic and mammalian homologs of these epitopes. Epitopes having a high predicted antigenicity were identified by prediction of hydrophobicity, surface probability and antigenic index using standard programs, including GCG and MacVector (Genetics Computer Group, University of Wisconsin Biotechnology Center, Madison, Wis.; Accelrys Inc., San Diego, Calif.). See also, Jameson and Wolf (1988), *Comput. Appl. Biosci.* 4:181-186.

CatSper3 immunogen preparations can be produced from crude extracts (e.g., microsomal fractions of cells expressing the proteins), from proteins or peptides substantially purified from cells which naturally or recombinantly express them or, for small immunogens, by chemical peptide synthesis. The CatSper3 immunogens can also be in the form of a fusion protein in which the non CatSper3 region is chosen for its adjuvant properties and/or the ability to facilitate purification.

The antibodies of the invention can be polyclonal or monoclonal, or can be antibody fragments, including Fab fragments, F(ab')2 fragments, Fv fragments, and single chain Fv fragments (scFv). In addition, after identifying useful antibodies by the method of the invention, recombinant antibodies can be generated, including any of the antibody fragments listed above, as well as chimeric and/or humanized antibodies based upon non-human antibodies to the CatSper3 proteins. In light of the present disclosure of CatSper3 proteins, as well as the characterization of other CatSper3 proteins enabled herein, one of ordinary skill in the art can produce the above-described antibodies by any of a variety of standard means. For an overview of antibody techniques, see Antibody Engineering, 2nd Ed., Borrebaek, ed., Oxford University Press, Oxford (1995).

As a general matter, monoclonal anti-CatSper3 antibodies can be produced by first injecting a mouse, rabbit, goat or other suitable animal with a CatSper3 immunogen in a suitable carrier or diluent. Carrier proteins or adjuvants can be utilized, and booster injections (e.g., bi- or tri-weekly over 8-10 weeks) can be employed as necessary. After allowing for development of a humoral response, the animals are sacrificed and their spleens are removed and resuspended in an appropriate buffer (e.g., phosphate buffered saline). The spleen cells serve as a source of lymphocytes, some of which will produce antibodies of the appropriate specificity. These cells are then fused with an immortalized cell line (e.g., a myeloma), and the products of the fusion are plated into tissue culture wells in the presence of a selective agent (e.g., HAT). The wells are serially screened and replated, selecting cells making a useful antibody each time. Typically, several screening and replating procedures are carried out until the wells contain single clones which are positive for antibody production. Monoclonal antibodies produced by such clones can be purified by standard methods such as affinity chromatography using Protein A Sepharose, by ion-exchange chromatography, or by variations and combinations of these techniques.

Antibodies of the invention can be used in a variety of applications. For example, antibodies can be used in a purification process (i.e., immunoaffinity purification) for CatSper3 proteins, in assays to detect the presence or level of CatSper3 protein in sperm (e.g., in a diagnostic test for a CatSper3-related disorder), or in assays to measure the presence or level of CatSper3 expression in transformed cells (e.g., in assays for regulators of CatSper3 expression, in Western blotting to identify cells expressing CatSper3 proteins, or in immunocytochemistry or immunofluorescence techniques to establish the cellular or extracellular location of CatSper3 proteins).

The antibodies of the invention can be bound or conjugated with other compounds or materials for diagnostic and/or therapeutic uses. For example, they can be coupled to labels such as radionuclides, fluorescent compounds (e.g., rhodamine), or enzymes for imaging or therapy. The labels can be bound to the antibodies covalently or non-covalently.

In another aspect, the invention provides kits for detecting at least an epitope of a CatSper3 protein. The kits include an anti-CatSper3 antibody and a means for detecting the antibody. The means for detecting the antibody can be a detectable label bound to the antibody or secondary antibodies for detecting the anti-CatSper3 antibodies (e.g., a labeled goat anti-rabbit-Ig antibody as a secondary antibody for detecting a rabbit anti-CatSper3 antibody).

Assays for Modulators of CatSper3 Expression or Activity.

In another aspect, the present invention provides assays for modulators of CatSper3 expression or activity. The modulators can affect the transcription, translation, post-translational processing, localization, or activity of the CatSper3 gene and/or protein.

Thus, in one series of embodiments, the transformed cells of the invention are contacted with a candidate compound, and the effect of the compound on the expression or activity of CatSper3 is determined. As a general matter, the assays require contacting a candidate compound with a cell expressing a CatSper3 protein and measuring an indicator of CatSper3 activity in the cell. The indicator can be an indicator of transcription (e.g., mRNA levels), translation (e.g., protein levels), post-translational processing (e.g., specific glycosylation), localization (e.g., immunohistochemistry), or activity (e.g., sodium or other monovalent ion flux; calcium or other divalent ion flux). The indicator measurement is then compared to a reference level to determine whether the candidate compound caused an increase or decrease in the indicator. The reference level can be extrinsic (e.g., a predetermined baseline level) or intrinsic (e.g., a measurement of the same cell prior to contact with the candidate compound). If an increase or decrease is significant (based on a single reading or on multiple readings from one or more cells), the candidate compound is identified as a potential modulator of CatSper3 activity. Assays for changes in CatSper3 activity can include any of those used routinely in the art for other genes. For example, changes in the presence or levels of CatSper3 mRNA or protein can be detected to identify enhancers or repressors of CatSper3 expression. Alternatively, when using a reporter gene construct of the invention, the biochemical or phenotypic change characteristic of the reporter can be used as an indication that the candidate compound enhances or represses reporter gene expression. In other embodiments, changes in the activity of the CatSper3 protein can be detected by measuring, for example, the flux of cations mediated by the CatSper3 protein, or by measuring whole cell or channel currents. Measurements of ion fluxes can be facilitated by the use of chromophores which change color depending upon the concentration of specific ions. The effects of candidate compounds on mature sperm cells can be tested to confirm or validate results obtained in the transformed cells of the invention.

Compounds which bind to CatSper3 are candidates for modulating CatSper3 activity. Thus, in another series of embodiments, libraries of compounds can be screened to identify candidates for modulating CatSper3 activity by contacting candidate compounds with a CatSper3 protein, or at least a structural domain of a CatSper3 protein, to identify compounds that bind to CatSper3. CatSper3 structural domains which can be used in these methods include those described above (i.e., transmembrane domains, extracellular loops, pore regions), but extracellular loops and pore regions are preferred. In such methods, the CatSper3 protein or CatSper3 structural domain can be immobilized (e.g., on a column or microparticle) and a solution of the candidate compound can be contacted with the CatSper3 moiety, or the candidate compound can be immobilized (e.g., on a column or microparticle) and a solution of the CatSper3 moiety can be contacted with the candidate compound. Alternatively, in some embodiments, neither the candidate compound nor the CatSper3 moiety is immobilized but, rather, both are in solution and binding is detected by, for example, aggregation of particles bearing the binding partners. Binding can be detected by methods well known in the art (e.g., radioactive or fluorescent labeling of one component of the potential binding pair; plasmon-resonance detection of binding; turbidity changes in aggregation assays). Compounds which, under physiological conditions (e.g., within the testis or epididymis, or within the vagina, uterus or fallopian tubes), exhibit significant binding (e.g., $K_d \leq 10$ μM) to a CatSper3 protein, are potential modulators of CatSper3 activity.

Methods of Modulating Fertility.

The CatSper3 gene and protein are ideal targets for potential contraceptive drugs. The restricted localization of CatSper3 to mature sperm means that a specific blocker should not affect other tissues and thus side effects should be low or nonexistent. Finally, since the channel represents a novel structure, it may be an excellent target for new channel agonists or antagonists.

Thus, in another aspect, the present invention provides methods of decreasing fertility by decreasing the expression or activity of a CatSper3 gene or protein. Such decreases in expression or activity can be achieved by means of a small molecule which represses expression of a CatSper3 gene, by means of an antisense molecule which inhibits the translation of a CatSper3 mRNA, by means of a small molecule that interferes with CatSper3 translation or post-translational processing, by means of a small molecule that interferes with CatSper3 localization, or by means of a molecule which blocks CatSper3 activity as an ion channel. Antibodies, including antibody fragments such as Fab fragments, F(ab')2 fragments, Fv fragments, and single-chain Fv fragments (ScFv), also can be used to inhibit CatSper3 activity by binding to extracellular domains of the protein and thereby block its activity.

Because most repressors or antagonists of CatSper3 expression or activity will be reversible or will affect only mature sperm, the effects of such compounds on fertility will be reversible because the molecules will be cleared from the body over time and new sperm are constantly being produced. Thus, repressors or antagonists of CatSper3 expression or activity can be used as human contraceptives because they can cause reversible infertility. Such contraceptives can be taken orally or parenterally (e.g., injection, transdermal patch, or bioerodable implant) by females if they achieve sufficient concentrations in the vagina, uterus or fallopian tubes to effectively inhibit CatSper3 activity and thereby decrease sperm motility and the ability of sperm to penetrate the ZP. Similarly, such contraceptives can be taken orally or parenterally by males if they achieve sufficient concentration in the testes or seminal fluids to effectively inhibit CatSper3 expression or activity, and thereby decrease sperm motility and the ability of sperm to penetrate the ZP. Alternatively, such compounds can be formulated into lubricants, moisturizers, foams or jellies for use with prophylactics, cervical caps, or contraceptive vaginal sponges, foams or jellies.

In another series of embodiments, repressors or antagonists of CatSper3 genes and proteins can be used as contraceptives to treat non-human mammals. These embodiments are similar to those described above for human contraception. Such contraceptives can be used with respect to domesticated animals that are maintained as pets, with respect to other commercially valuable domesticated animals (e.g., cows, sheep, horses), or with respect to animal nuisances (e.g., mice, rats, raccoons, gophers). In some embodiments, the contraceptives are orally available and can be mixed into food sources for the animals. In other embodiments, the contraceptives can be administered parenterally (e.g., injection, transdermal patch, or bioerodable implant).

To the extent that the mammalian CatSper3 genes and proteins and the fish, amphibian and insect homologs of the CatSper3 genes and proteins share substantial sequence identity, repressors or antagonists of mammalian CatSper3 genes and proteins can also be used in the control of fish, amphibian and insect nuisances (e.g., mosquitoes). In addition, the non-mammalian homologs of the CatSper3 genes and proteins can be used to identify additional repressors and antagonists which are more specific or effective for such homologs.

Methods of CatSper3 Genotyping and Diagnosing CatSper3-Related Disorders.

In another aspect, the present invention provides methods for genotyping subjects with respect to the CatSper3 gene, and diagnosing CatSper3-related disorders such as infertility. Thus, for example, the CatSper3 nucleic acids (or a portion thereof) of a subject can be tested to ascertain whether that subject's CatSper3 genotype includes any mutations in the sequences relative to wild-type. Of particular significance would be mutations which introduce termination or frameshift mutations that prevent the production of functional CatSper3 proteins. Point mutations, however, can also be identified which cause decreased CatSper3 activity. Similarly, the antibodies of the present invention can be used to test the sperm of a subject to determine the presence or level of CatSper3 proteins. Of particular note would be an absence or significant decrease in the level of CatSper3 protein. Point mutations, however, can also cause infertility and can be detected by antibodies which are specific for epitopes including or affected by the mutant sequences. Determination of a subject's CatSper3 genotype can be used for genetic or reproductive counseling, or for diagnosing infertility that results from a CatSper3 defect.

To determine a subject's CatSper3 genotype, or for diagnosing a CatSper3-related disorder, the nucleic acids of the invention can be used as primers in polymerase chain reaction (PCR) (e.g., anchor PCR or RACE PCR), or ligase chain reaction (LCR) amplifications of the subject's DNA/mRNA. See, e.g., U.S. Pat. No. 4,683,195 and U.S. Pat. No. 4,683, 202; Landegran et al. (1988), *Science* 241:1077-1080; Nakazawa et al. (1994), *Proc. Natl. Acad. Sci. USA* 91:360-364; and Abravaya et al. (1995), *Nucleic Acids Res.* 23:675-682. Other useful methods for amplifying a subjects DNA/mRNA using the nucleic acids of the invention include self-sustained sequence replication (e.g., Guatelli et al. (1990), *Proc. Natl. Acad. Sci. USA* 87:1874-1878), transcriptional amplification (e.g., Kwoh et al. (1989), *Proc. Natl. Acad. Sci. USA* 86:1173-1177), and Q-Beta Replicase-based systems (e.g., Lizardi et al. (1988), *Bio/Technology* 6:1197. The presence, absence or size of the resulting amplification products (e.g., Saiki et al. (1986), *Nature* 324:163; Saiki et al. (1989), *Proc. Natl. Acad. Sci. USA* 86:6230; Gibbs et al. (1989), *Nucleic Acids Res.* 17:2437-2448; Prossner (1993), *Tibtech* 11:238; Gasparini et al. (1992), *Mol. Cell Probes* 6:1; Barany (1991), *Proc. Natl. Acad. Sci. USA* 88:189), direct sequencing of the amplification products (e.g., Maxim and Gilbert (1977), *Proc. Natl. Acad. Sci. USA* 74:560; Sanger (1977), *Proc. Natl. Acad. Sci. USA* 74:5463), and other standard analytic techniques can be employed to determine CatSper3 genotypes. The amplified products can also be used in many of the techniques described below.

The nucleic acids of the invention also can be used as probes in hybridization and/or conformation-based assays to identify complementary or imperfectly complementary sequences in a subject.

For example, in some embodiments, mutations can be identified by selectively hybridizing sample nucleic acids to immobilized control nucleic acids. The controls can be adsorbed to filters or columns, or can be arranged in high density ordered arrays containing hundreds or thousands of oligonucleotides probes (see, e.g., Cronin et al. (1996), *Human Mutation* 7:244-255; Kozal et al. (1996), *Nature Medicine* 2:753-759).

In other embodiments, enzymatic or chemical cleavage can be employed to cleave or restrict duplexes of sample and control sequences at mismatched bases (e.g., Myers et al. (1985), *Science* 230:1242). For example, RNA/DNA duplexes can be treated with RNAse and DNA/DNA hybrids can be treated with 51 nuclease to digest duplexes at mismatched bases, G/A mismatches are cleaved at the A by the *E. coli* mutY enzyme, G/T mismatches are cleaved at the T by the human thymidine DNA glycosylase (see, e.g., Hsu et al. (1994), *Carcinogenesis* 15:1657-1662). Chemical cleavage of mismatches can be employed using, for example, hydroxylamine, osmium tetroxide and/or piperidine. See generally, e.g., Cotton et al. (1988), *Proc. Natl. Acad. Sci. USA* 85:4397; Saleeba et al. (1992), *Methods Enzymol.* 217:286-295; and U.S. Pat. No. 5,459,039.

In other embodiments, mutations can create or destroy specific sequences which serve cleavage points for restriction enzymes or ribozymes. Thus, restriction fragment length polymorphism (RFLP) analysis can be employed in which (amplified) sample DNA is digested with at least one restriction endonuclease, and the resulting fragment lengths are analyzed and compared to controls to determine the presence or absence of mutations which affect the pattern of restriction fragment lengths. Similarly, sequence-specific ribozymes can be used to identify mutations that create or destroy ribozyme cleavage sites. See, e.g., U.S. Pat. No. 5,498,531.

In other embodiments, mutations can be detected by their effect on the electrophoretic mobility of a sequence, either as a single-stranded nucleic acid or as duplex. For example, single-strand conformation polymorphism (SSCP) analysis (Orita et al. (1989), *Proc. Natl. Acad. Sci. USA* 86:2766; Cotton (1993), *Mutat. Res.* 285:125-144; Hayashi (1992), *Genet. Anal. Tech. Appl.* 9:73-79; and Keen et al. (1991), *Trends Genet.* 7:5). denaturing gradient gel electrophoresis (DGGE) (Myers et al. (1985), *Nature* 313:495). and temperature gradient gel electrophoresis (Rosenbaum and Reissner (1987), *Biophys. Chem.* 265:12753) can be employed.

These and other methods of detecting mutations in the CatSper3 genes and proteins will be apparent to one of ordinary skill in the art based upon the nucleic acid and protein sequences disclosed herein.

In Vitro Fertilization.

In another aspect, the present invention provides a method of in vitro fertilization of ova by sperm characterized by decreased CatSper3 expression or activity. It has previously been shown that CatSper1-deficient sperm appear to be normal in all respects except in their motility and their ability to penetrate the ZP. Moreover, CatSper1-deficient sperm are capable of fertilizing ova from which the ZP has been removed. It is expected that CatSper3-deficient sperm will have similarly reduced motility and ability to fertilize ova with intact ZPs. Thus, the present invention provides a method of in vitro fertilization for CatSper3-deficient males in which the sperms of such males are treated to overcome the CatSper3 deficiency or are contacted with ova from which the ZP have been removed. Because other genetic deficiencies can result in sperm which are incapable of penetrating the ZP, this method can be extended to other males having genetic deficiencies which affect ZP-penetration or for which in vitro fertilization previously has been unsuccessful using ova with intact ZPs.

Methods of Treating CatSper3-Mediated Infertility.

In another aspect, the present invention provides methods of treating infertility in CatSper3-deficient males, in which an enhancer of CatSper3 expression or an agonist of CatSper3 activity is administered to the subject. In other embodiments, gene or protein therapy can be employed to provide the CatSper3 gene or protein to sperm (or sperm progenitors) which are deficient in the CatSper3 gene or protein. For gene therapy, a genetic construct encoding a CatSper3 protein can be employed to cause expression of a CatSper3 protein in sperm or sperm progenitors which are deficient in the CatSper3 gene or protein.

In another aspect, infertility of a mating pair (e.g., a human couple) can result from antibodies generated by the female against antigens present on the sperm of the male. In some cases, the antibodies can be directed against an epitope of a CatSper3 protein. Thus, the present invention also provides methods of diagnosing an anti-CatSper3 antibody-mediated infertility caused by anti-CatSper3 antibodies present in a female urogenital tract. The methods include obtaining a sample of antibodies present in the female and contacting the antibodies with CatSper3 proteins or fragments of CatSper3 proteins. In some embodiments, the CatSper3 fragments are epitopes of the CatSper3 proteins having high predicted antigenicity (e.g., high predicted antigenicity epitopes of SEQ ID NO: 2, or high predicted antigenicity epitopes (e.g., residues 386-407) of SEQ ID NO: 4, and allelic and mammalian homologs thereof). In these methods, either the female's antibodies or the CatSper3 proteins/fragments optionally can be immobilized and either the female's antibodies or the CatSper3 proteins/fragments optionally can be detectably labeled to facilitate detection of binding between the antibodies and the CatSper3 proteins/fragments.

In these cases, administering an excess of the CatSper3 protein, or at least a fragment of the CatSper3 protein including the relevant epitope, can saturate the binding sites of the anti-CatSper3 antibodies present in the female's urogenital tract and thereby inhibit or reduce the antibody-mediated infertility. Alternatively, an anti-idiotypic antibody (i.e., an antibody which specifically binds to the variable regions of another antibody with a defined specificity) can be employed. That is, an antibody which binds specifically to anti-CatSper3 antibodies can be employed to inhibit the anti-CatSper3 antibodies present in the female's urogenital tract and thereby inhibit or reduce the antibody-mediated infertility. One of ordinary skill in the art can easily identify the relevant CatSper3 epitopes recognized by such female antibodies (e.g., using the methods described above) and produce substantially pure preparations of the relevant epitope or anti-idiotypic antibodies by standard means. Thus, the invention also provides methods for treating an anti-CatSper3 antibody-mediated infertility caused by anti-CatSper3 antibodies present in a female urogenital tract. The methods include administering into the urogenital tract of the female an amount of the relevant CatSper3 epitope (or whole CatSper3 protein) or an amount an anti-idiotypic antibody effective to inhibit the anti-CatSper3 antibodies and thereby inhibit or reduce the antibody-mediated infertility.

Business Methods Relating to CatSper3.

In another aspect, the present invention provides a method of conducting a drug discovery business comprising: identifying, by the assays of the invention, one or more agents which antagonize CatSper3 activity; determining if an agent identified in such an assay, or an analog of such an agent, inhibits at least one of sperm motility or egg penetrance; conducting therapeutic profiling of an agent identified as an antagonist for efficacy and toxicity in one or more animal models; and formulating a pharmaceutical preparation including one or more antagonist agents identified as having an acceptable therapeutic profile.

In one embodiment, the drug discovery business further includes the step of establishing a system for distributing the pharmaceutical preparation for sale, and can optionally include establishing a sales group for marketing the pharmaceutical preparation.

In another aspect, the present invention provides a method of conducting a drug discovery business comprising: identifying, by the subject assay, one or more agents which agonize CatSper3 activity; determining if an agent identified in such an assay, or an analog of such an agent, increases at least one of sperm motility or egg penetrance; conducting therapeutic profiling of an agent identified as an agonist for efficacy and toxicity in one or more animal models; and formulating a pharmaceutical preparation including one or more agents identified as having an acceptable therapeutic profile.

In certain embodiments, the drug discovery business further includes the step of establishing a system for distributing the pharmaceutical preparation for sale, and can optionally include establishing a sales group for marketing the pharmaceutical preparation.

In certain embodiments, the assay to identify agents which agonize CatSper3 activity is conducted using wild type CatSper3. In another embodiment, the assay to identify agents which agonize CatSper3 activity is conducted using a mutant CatSper3. By a mutant CatSper3 is meant to include a CatSper3 polypeptide containing one or more insertions, deletions, or substitutions in amino acid sequence, wherein said insertions, deletions, or substitutions change the activity of the mutant CatSper3 in comparison to wild type CatSper3. Such a change in activity includes, but is not limited to, a change in motility, egg penetrance, cation transport. A change in activity would also include a change in the proper localization or expression of the CatSper3 protein or mRNA.

In still another aspect, the invention provides a method of conducting a reproductive medicine business comprising: examining a sperm sample from a male patient, wherein said patient is experiencing a fertility problem; determining if said sperm are characterized by at least one of a decrease in motility or a decrease in egg penetrance; performing in vitro analysis to determine the efficacy of a CatSper3 agonist in increasing at least one of sperm motility or egg penetrance; establishing a treatment regimen comprising administering an amount of a CatSper3 agonist effective to increase at least one of sperm motility or egg penetrance in said male.

In certain embodiments, the method further includes a step wherein said male patient is monitored by a physician to evaluate improvement in fertility. Such evaluation can include examination of sperm at regular intervals following the initiation of treatment to measure improvements in one or more of sperm motility or egg penetrance. The frequency of follow-up evaluation by the treating physician will be determined by the physician or a trained health care provider. Factors to consider are the patient's schedule and comfort level, as well as the urgency with which a male patient is attempting to father an offspring. Representative follow-up appointments can be conducted weekly, semi-weekly, or monthly. In another embodiment, the method further includes the step of billing the patient or the patient's insurance provider. We note that in cases where the patient's health insurance is paying for all or a portion of said fertility treatments, the policies of said health insurance provider will likely influence the frequency of follow-up appointments.

In yet another aspect, the present invention provides a method of conducting a contraceptive medicine business comprising: providing a pharmaceutical preparation discovered through the methods of a drug discovery business, wherein said preparation inhibits the activity of CatSper3; providing instructions to physicians and health care providers for the administration of an amount of said pharmaceutical preparation effective to inhibit the activity of CatSper3, wherein said effective amount is sufficient to prevent pregnancy.

In one embodiment, the method further includes the step of establishing a system for distributing the pharmaceutical preparation for sale, and can optionally include establishing a sales group for marketing the pharmaceutical preparation.

CatSper3 encodes a cation channel. Numerous types of cation channels play critical roles in cellular processes including regulation of cardiac function (e.g., calcium channels). Thus, a great limitation of methods which employ administration of agents which either increase or decrease the activity of cation channels is that such methods are likely to have substantial side-effects. These side-effects can include significant cardiac complications. However, as disclosed herein, CatSper3 is specifically expressed in sperm. Accordingly, agents which increase or decrease the activity of CatSper3 can be administered to patients without the side effects associated with either general cation channel antagonists and agonists, or antagonists and agonists of cation channels which are more widely expressed in the body.

Through a drug discovery business, one or more agents which can antagonize the activity of CatSper3 can be identified. By antagonize the activity is meant to decrease, in whole or in part, the activity of CatSper3. Such a decrease in activity can be measured by examining at least one of sperm motility, egg penetrance, or cation transport. The terms decrease and antagonize will be used interchangeably throughout.

In certain embodiments, the initially identified CatSper3 agonist or antagonist can be subjected to further lead optimization, e.g., to further refine the structure of a lead compound so that potency and activity are maintained but balanced with important pharmacological characteristics including:
Solubility
Permeability
Bioavailability
Toxicity
Mutagenicity
Pharmacokinetics—absorption, distribution, metabolism, elimination of the drug Structural modifications are made to a lead compound to address issues with the parameters listed above. These modifications however, must take into account possible effects on the molecule's potency and activity. For example, if the solubility of a lead compound is poor, changes can be made to the molecule in an effort to improve solubility; these modifications, however, can negatively affect the molecule's potency and activity. SAR data are then used to determine the effect of the change upon potency and activity. Using an iterative process of structural modifications and SAR data, a balance is created between these pharmacological parameters and the potency and activity of the compound.

Candidate antagonists, or combinations thereof, must them be tested for efficacy and toxicity in animal models. Such therapeutic profiling is commonly employed in the pharmaceutical arts. Before testing an experimental drug in humans, extensive therapeutic profiling (e.g., preclinical testing) must be completed to establish initial parameters for safety and efficacy. Preclinical testing establishes a mechanism of action for the drug, its bioavailability, absorption, distribution, metabolism, and elimination through studies performed in vitro (that is, in test tubes, beakers, petri dishes, etc.) and in animals. Animal studies are used to assess whether the drug will provide the desired results. Varying doses of the experimental drug are administered to test the drug's efficacy, identify harmful side-effects that may occur, and evaluate toxicity.

Briefly, one of skill in the art will recognize that the identification of a candidate agent which antagonizes CatSper3 activity in a drug based screen is a first step in developing a pharmaceutical preparation useful as a contraceptive agent. Administration of an amount of said pharmaceutical preparation effective to successfully prevent pregnancy (i.e., to act as a useful contraceptive agent) must be both safe and effective. Early stage drug trials, routinely used in the art, help to address concerns of the safety and efficacy of a potential pharmaceutical. In the specific case of a CatSper3 antagonist, efficacy of the pharmaceutical preparation could be readily evaluated in a mouse or rat model. Briefly, male mice could be administered varying doses of said pharmaceutical preparations over various time schedules. Control male mice can be administered a placebo (e.g., carrier or excipient alone). The male mice are then allowed to mate freely by placing said male into cages with female mice, and measuring rate of conception over time. Given the efficacy of currently available forms of birth control, an effective contraception should be at least 80% effective, preferably 85% effective, more preferably 90% effective, most preferably 95%, 96%, 97%, 98%, 99% or greater than 99% effective in preventing pregnancy.

In one embodiment, the step of therapeutic profiling includes toxicity testing of compounds in cell cultures and in animals; analysis of pharmacokinetics and metabolism of the candidate drug; and determination of efficacy in animal models of diseases. In certain instances, the method can include analyzing structure-activity relationship and optimizing lead structures based on efficacy, safety and pharmacokinetic profiles. The goal of such steps is the selection of drug candidates for pre-clinical studies to lead to filing of Investigational New Drug ("IND") applications with the U.S. FDA and/or similar applications with similar regulatory authorities prior to human clinical trials.

Between lead optimization and therapeutic profiling, one goal of the subject method is to develop a CatSper3 agonist or antagonist which has minimal side-effects. In the case of antagonists, the lead compounds will have clinically acceptable effects on vasodilatation (i.e., dizziness, hypotension, headache, flushing, edema, etc.), myocardial ischemia, hypotension, bradycardia, transient asystole, exacerbation of heart failure, ventricular dysfunction, SA node or AV conduction disturbances, or plasma digoxin levels.

By "toxicity profiling" is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made during the regulatory approval process. This determination does not follow hard and fast rules, and that which is considered an acceptable side effect varies due to factors including: (a) the severity of the condition being treated, and (b) the availability of other treatments and the side-effects currently associated with these available treatments. For example, the term cancer encompasses a complex family of disease states related to mis-regulated cell growth, proliferation, and differentiation. Many forms of cancer are particularly devastating diseases which cause severe pain, loss of function of the effected tissue, and death. Chemotherapeutic drugs are an important part of the standard therapy for many forms of cancer. Although chemotherapeutics themselves can have serious side-effects including hair-loss, severe nausea, weight-loss, and sterility, such side-effects are considered acceptable given the severity of the disease they aim to treat.

In contrast, however, most currently available forms of birth control do not have significant side-effects. Thus, a pharmaceutical preparation of a CatSper3 antagonist should have minimal toxicity and side-effects. Toxicity tests can be conducted in tandem with efficacy tests, and male mice administered effective doses of the pharmaceutical preparation can be monitored for adverse reactions to the preparation. Potential adverse reactions associated with a contraceptive agent may include loss of sex drive and behavioral changes. Blood, urine, and fecal samples taken from treated mice can also be monitored to detect any potential adverse changes in immune, kidney, or liver function. Additionally, given that CatSper3 is a cation channel, mice receiving said pharmaceutical preparation should also be monitored for any changes in cardiac function indicative of cross reactivity of the CatSper3 antagonist with other cation channels.

Agents which antagonize CatSper3 activity, and which are proven safe and effective in animal studies, can be formulated into a pharmaceutical preparation. Such pharmaceutical preparations can then be marketed, distributed, and sold as contraceptive agents.

Given the link between loss of CatSper3 activity and fertility, there is substantial utility in agents which increase the activity of CatSper3 to treat male fertility problems. Many instances of infertility involve problems linked to the male. Such male infertility issues include low sperm count, poor sperm motility, and abnormal sperm morphology. Currently there are few effective treatments for male-associated infertility.

The first step in developing potentially successful treatments for male infertility is the identification of CatSper3 agonists. A CatSper3 agonist is one or more agents which increase the activity of CatSper3. As explained above with respect to CatSper3 antagonists, agonists of the CatSper3 protein are also expected to have fewer potential side-effects than other cation channel agonists.

Methods for identifying agents which act as CatSper3 agonists are performed largely as detailed for CatSper3 antagonists. However, a preferred CatSper3 agonist will increase one or more of sperm motility or egg penetrance. Additionally, we note that when identifying a CatSper3 agonist, such an agent can agonize the activity of a wild type CatSper3. In addition, or alternatively, such an agent can agonize the activity of a mutant CatSper3. One or more agonists identified by these methods can then be tested for safety and efficacy, as outline in detail above. Agents which are shown to be safe and effective in animal studies are formulated into a pharmaceutical preparation.

We note that said CatSper3 agonists are not likely to be effective for treating all male fertility problems. However, it is expected that some undetermined percentage of male fertility problems will be amenable to treatment using agonists of CatSper3 function. For example, a certain percentage of male infertility which results in poor sperm motility is likely due to mutations in CatSper3. Given that CatSper3 is expressed specifically in sperm, males possessing such a mutation would be expected to have little or no additional medical problems, and this explains in part why infertility is often found in otherwise healthy men. Additionally, a CatSper3 agonist can improve sperm motility overall, and thus help compensate for poor sperm motility due to other unrelated causes.

Conducting a Reproductive Medicine Business.

A pharmaceutical preparation including one or more agents which agonize the activity of a wild type or mutant CatSper3 can be useful in establishing a reproductive medicine business which provides treatment for candidate male patients experiencing fertility difficulties. Sperm samples provided by male patients are examined to determine if infertility in said male patients may be amenable to treatment with the pharmaceutical preparation. Patients whose sperm is characterized by a decrease in at least one of motility or egg penetrance may be eligible for treatment. Prior to treatment, sperm samples provided by the male patients are tested in vitro with the pharmaceutical preparation to further assess whether said male is eligible for treatment. This additional step of in vitro testing helps to alleviate unnecessary treatment in males whose infertility is unlikely to be improved with the CatSper3 agonist.

Male patients whose sperm shows increased motility or egg penetrance in vitro are eligible for fertility treatment including the pharmaceutical preparation including one or more CatSper3 agonist. The exact treatment regimen will vary from patient to patient, and can be readily determined by an experienced medical professional. However, the treatment regimen will include administration of an amount of said pharmaceutical preparation effective to increase at least one of sperm motility or egg penetrance in said treated male. In a preferred embodiment, the increase in sperm motility or egg penetrance will result in an increase in fertility.

Pharmaceutical Preparations.

Pharmaceutically acceptable preparations comprising a therapeutically effective amount of one or more of the identified agents (i.e., antagonists or agonists) described above, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds can be simply dissolved or suspended in sterile water.

The phrase "therapeutically effective amount" as used herein means that amount of an agent or composition which is effective for producing some desired therapeutic effect, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, the pharmaceutical preparation is non-pyrogenic, i.e., does not elevate the body temperature of a patient.

The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977), *J. Pharm. Sci.* 66: 1-19.)

The pharmaceutically acceptable salts of the subject agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the agents of the present invention can contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. (1977), supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations can conveniently be presented in unit dosage form and can be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1% to about 99% of active ingredient, preferably from about 5% to about 70%, most preferably from about 10% to about 30%.

Methods of preparing these formulations or compositions include the step of bringing into association one or more agents of the present invention with the carrier and, optionally, one or more accessory ingredients. In general, the formulations are prepared by uniformly and intimately bringing into association one or more agents of the present invention with liquid carriers, or finely divided solid carriers, or both, and then, if necessary, shaping the product.

Formulations of the invention suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A agent of the present invention can also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration can be presented as a suppository, which can be prepared by mixing one or more agents of the invention with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of one or more agents of this invention include powders, sprays, ointments, pastes, creams, lotions, gels, solutions, patches and inhalants. The active agents can be mixed under sterile conditions with a pharmaceutically acceptable carrier, and with any preservatives, buffers, or propellants which can be required.

The ointments, pastes, creams and gels can contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an agent of the present invention to the body. Such dosage forms can be made by dissolving or dispersing the subject compound in the proper medium. Absorption enhancers can also be used to increase the flux of the subject agent across the skin. The rate of such flux can be controlled by either providing a rate controlling membrane or dispersing the compound in a polymer matrix or gel.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

EQUIVALENTS

While this invention has been particularly shown and described with references to preferred embodiments thereof, it will be understood by those skilled in the art that various changes in form and details may be made therein without departing from the spirit and scope of the invention. Those skilled in the art will recognize, or be able to ascertain using no more than routine experimentation, many equivalents to the specific embodiments of the invention described specifically herein. Such equivalents are intended to be encompassed in the scope of the invention.

We claim:

1. A method of selecting a compound having potential contraceptive activity, the method comprising:
   (a) contacting a candidate compound with a cell expressing a CatSper3 protein, the CatSper3 protein comprising at least 90% similarity to the amino acid sequence of SEQ ID NO: 2, and wherein the CatSper3 protein has CatSper3 activity;
   (b) measuring an indicator of CatSper3 activity in said cell, wherein the indicator is selected from the group consisting of the level of mRNA encoding the CatSper3 protein, the level of CatSper3 protein, cation flux across a membrane of the cell, whole cell currents of the cell, and channel currents of the cell;
   (c) determining whether said candidate compound caused a decrease in CatSper3 activity in said cell relative to CatSper3 activity prior to contact with the candidate compound; and
   (d) selecting said candidate compound that causes a decrease in CatSper3 activity as having potential contraceptive activity.

2. The method as in claim 1, wherein said cell has been transformed with a genetic construct capable of expressing a CatSper3 protein.

3. A method of selecting a compound that inhibits sperm motility, the method comprising:
   (a) contacting a candidate compound with a cell that has been transformed with a genetic construct capable of expressing a CatSper3 protein, the CatSper3 protein comprising at least 90% similarity to the amino acid sequence of SEQ ID NO: 2, and wherein the CatSper3 protein has CatSper3 activity;
   (b) measuring an indicator of CatSper3 activity in the cell, wherein the indicator is selected from the group consisting of the level of mRNA encoding the CatSper3 protein, the level of CatSper3 protein, cation flux across a membrane of the cell, whole cell currents of the cell, and channel currents of the cell;
   (c) determining whether the candidate compound caused a decrease in CatSper3 activity in the cell relative to CatSper3 activity prior to contact with the candidate compound;
   (d) contacting said candidate compound with normal sperm if said candidate compound causes a decrease in CatSper3 activity in the cell; and
   (e) selecting said candidate compound that causes a decrease in sperm motility as inhibiting sperm motility.

4. A method of selecting a compound having potential contraceptive activity, the method comprising:
   (a) contacting normal sperm with a candidate compound previously identified as causing a decrease in CatSper3 activity in a cell, the CatSper3 protein comprising at least 90% similarity to the amino acid sequence of SEQ ID NO: 2, and wherein the CatSper3 protein has CatSper3 activity;
   (b) assaying for a decrease in sperm motility relative to sperm motility in the cell prior to contact with the candidate compound; and
   (c) selecting said candidate compound that causes a decrease in sperm motility as having potential contraceptive activity.

5. The method of claim 4, wherein said candidate compound was previously identified as causing a decrease in CatSper3 activity in a cell by the steps comprising:
   (1) contacting a candidate compound with a cell expressing a CatSper3 protein, the CatSper3 protein comprising at least 90% similarity to the amino acid sequence of SEQ ID NO:2, and wherein the CatSper3 protein has CatSper3 activity;
   (2) measuring an indicator of CatSper3 activity in the cell, wherein the indicator is selected from the group consisting of the level of mRNA encoding the CatSper3 protein, the level of CatSper3 protein, cation flux across a membrane of the cell, whole cell currents of the cell, and channel currents of the cell;
   (3) determining whether the candidate compound caused a decrease in CatSper3 activity in the cell relative to CatSper3 activity prior to contact with the candidate compound; and
   (4) identifying the candidate compound as causing a decrease in CatSper3 activity in the cell.

6. The method of claim 4, wherein said candidate compound was previously identified as causing a decrease in CatSper3 activity in a cell by the steps comprising:
   (1) contacting a cell expressing a CatSper3 protein with at least one candidate compound from a library, the CatSper3 protein comprising at least 90% similarity to the amino acid sequence of SEQ ID NO:2, and wherein the CatSper3 protein has CatSper3 activity;
   (2) measuring an indicator of CatSper3 activity in the cell, wherein the indicator is selected from the group consisting of the level of mRNA encoding the CatSper3 protein, the level of CatSper3 protein, cation flux across a membrane of the cell, whole cell currents of the cell, and channel currents of the cell;
   (3) determining whether the candidate compound caused a decrease in CatSper3 activity in the cell relative to CatSper3 activity prior to contact with the candidate compound;
   (4) toxicity profiling the candidate compound; and
   (5) identifying the candidate compound from the library as causing a decrease in CatSper3 activity in the cell.

7. A method of selecting a compound having potential contraceptive activity, the method comprising:
   (a) contacting a candidate compound with a cell expressing a CatSper3 protein, the CatSper3 protein comprising at least 90% similarity to the amino acid sequence of SEQ ID NO: 2, and wherein the CatSper3 protein has CatSper3 activity;
   (b) measuring an indicator of CatSper3 activity in the cell, wherein the indicator is selected from the group consisting of the level of mRNA encoding the CatSper3 protein, the level of CatSper3 protein, cation flux across a membrane of the cell, whole cell currents of the cell, and channel currents of the cell;

(c) determining whether said candidate compound caused a decrease in CatSper3 activity in the cell relative to CatSper3 activity prior to contact with the candidate compound;

(d) toxicity profiling the candidate compound; and (e) selecting said candidate compound that causes a decrease in CatSper3 activity as having potential contraceptive activity.

8. The method as in claim 7, wherein toxicity profiling is performed in an animal.

9. The method as in claim 8, wherein toxicity profiling is performed by monitoring the animal for adverse changes in at least one of immune function, kidney function, liver function, and cardiac function.

10. A method of selecting a compound that inhibits sperm motility, the method comprising:

(a) contacting a cell expressing a CatSper3 protein with at least one candidate compound from the library, the CatSper3 protein comprising at least 90% similarity to the amino acid sequence of SEQ ID NO: 2, and wherein the CatSper3 protein has CatSper3 activity;

(b) measuring an indicator of CatSper3 activity in the cell, wherein the indicator is selected from the group consisting of the level of mRNA encoding the CatSper3 protein, the level of CatSper3 protein, cation flux across a membrane of the cell, whole cell currents of the cell, and channel currents of the cell;

(c) determining whether the step of contacting caused a decrease in CatSper3 activity in the cell relative to CatSper3 activity prior to contact with the candidate compound;

(d) toxicity profiling the candidate compound;

(e) contacting said candidate compound with normal sperm if said candidate compound causes a decrease in CatSper3 activity in the cell; and (f) selecting said candidate compound that causes a decrease in sperm motility as inhibiting sperm motility.

* * * * *